United States Patent
Young et al.

(10) Patent No.: US 6,375,930 B2
(45) Date of Patent: *Apr. 23, 2002

(54) MEMBRANE INCORPORATION OF TEXAPHYRINS

(75) Inventors: Stuart W. Young, Portola; Meredith Wright, San Jose, both of CA (US); Jonathan L. Sessler, Austin, TX (US); Tarak D. Mody, Sunnyvale; Darren Magda, Cupertino, both of CA (US)

(73) Assignees: Board of Regents, The University of Texas System, Austin, TX (US); Pharmacyclics, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/975,090

(22) Filed: Nov. 20, 1997

Related U.S. Application Data

(63) Continuation of application No. PCT/US97/09501, filed on Jun. 4, 1997.
(60) Provisional application No. 60/056,917, filed on Jun. 4, 1996.

(51) Int. Cl.$^7$ ............................................. A61B 55/055
(52) U.S. Cl. .................. 424/9.362; 424/1.11; 424/1.65; 424/9.1; 424/9.3; 424/450; 546/11; 544/1; 540/1; 540/145
(58) Field of Search ................................. 424/1.11, 1.65, 424/9.1, 9.3, 9.362, 9.4, 9.5, 9.6, 9.7, 9.8, 450; 540/1, 121, 145; 544/1, 224; 546/1, 152, 184, 249; 548/100, 300.1

(56) References Cited

U.S. PATENT DOCUMENTS

| | | | |
|---|---|---|---|
| 4,193,983 A | * 3/1980 | Ullman et al. | ............... 424/1.11 |
| 4,478,824 A | 10/1984 | Franco et al. | |
| 4,931,276 A | 6/1990 | Franco et al. | |
| 4,935,498 A | 6/1990 | Sessler et al. | ................. 534/15 |
| 5,000,960 A | 3/1991 | Wallach | ....................... 424/450 |
| 5,252,720 A | 10/1993 | Sessler et al. | ................. 534/11 |
| 5,257,970 A | 11/1993 | Dougherty | |
| 5,258,453 A | 11/1993 | Kopecek et al. | |
| 5,328,678 A | 7/1994 | Fugii et al. | |
| 5,445,608 A | 8/1995 | Chen et al. | |
| 5,457,183 A | 10/1995 | Sessler et al. | |
| 5,466,438 A | 11/1995 | Unger et al. | |
| 5,559,207 A | 9/1996 | Sessler et al. | ............... 530/300 |
| 5,565,552 A | 10/1996 | Magda et al. | .................. 534/11 |
| 5,567,687 A | 10/1996 | Magda et al. | .................. 514/44 |
| 5,587,463 A | 12/1996 | Sessler et al. | ................. 534/15 |
| 5,591,422 A | * 1/1997 | Hemmi et al. | ........... 424/9.362 |
| 5,594,136 A | 1/1997 | Sessler et al. | ............... 540/472 |
| 5,595,726 A | 1/1997 | Magda et al. | .............. 424/9.61 |
| 5,599,923 A | 2/1997 | Sessler et al. | ............... 540/145 |
| 5,599,928 A | 2/1997 | Hemmi et al. | ............... 540/474 |
| 5,607,924 A | 3/1997 | Magda et al. | .................. 514/44 |
| 5,622,946 A | 4/1997 | Sessler et al. | ............... 514/185 |
| 6,072,038 A | * 6/2000 | Sessler et al. | ........... 530/391.7 |

FOREIGN PATENT DOCUMENTS

| | | |
|---|---|---|
| EP | 0 616 801 A1 | 9/1994 |
| WO | WO 90/10633 | 9/1990 |
| WO | WO 92/05109 | 4/1992 |
| WO | 94/29316 | 12/1994 |
| WO | WO95/10307 | 4/1995 |
| WO | 95/21845 | 8/1995 |
| WO | 96/09315 | 3/1996 |
| WO | WO 96/32094 | 10/1996 |
| WO | WO97/46262 | 12/1997 |

OTHER PUBLICATIONS

Mathews et al, Biochemistry, pp. 307 & 633–634, 1990.*
Sessler et al., "Synthesis and Crystal Structure of a Novel Tripyrrane–Containing Porphyrinogen–like Macrocycle", *J. Org. Chem.*, 52:4394–4397, 1987.
Sessler et al., "The Coordination Chemistry of Planar Pentadentate "Porphyrin–Like" Ligands", *Comm. Inorg. Chem.*, 7:333–350, 1988.
Sessler et al., "An "Expanded Porphyrin": The Synthesis and Structure of a New Aromatic Pentadentate Ligand", *J. Am. Chem. Soc.*, 110:5586–5588, 1988.
Sessler et al., "A Water–Stable Gadolinium (III) Complex Derived from a New Pentadentate "Expanded Porphyrin" Ligand", *Inorg. Chem.*, 28:3390–3393, 1989.
Sessler et al., "Binding of Pyridine and Benzimidazole to a Cadmium "Expanded Porphyrin": Solution and X–ray Structural Studies", *Inorg. Chem.*, 28:1333–1341, 1989.
Harriman et al., "Metallotexaphyrins: A New Family of Photosensitisers for Efficient Generation of Singlet Oxygen", *J. Chem. Soc., Chem. Commun.*, 314–316, 1989.

(List continued on next page.)

*Primary Examiner*—Dameron L. Jones
(74) *Attorney, Agent, or Firm*—Vinit G. Kathardekar

(57) ABSTRACT

Compositions having a texaphyrin-lipophilic molecule conjugate loaded into a biological vesicle and methods for imaging, diagnosis and treatment using the loaded vesicle are provided. For example, liposomes or red blood cells loaded with a paramagnetic texaphyrin-lipophilic molecule conjugate have utility as a blood pool contrast agent, facilitating the enhancement of normal tissues, magnetic resonance angiography, and marking areas of damaged endothelium by their egress through fenestrations or damaged portions of the blood vascular system. Liposomes or cells loaded with a photosensitive texaphyrin-lipophilic molecule conjugate can be photolysed, allowing for a photodynamic therapy effect at the site of lysis. Availability of red blood cells loaded with a photosensitive texaphyrin-lipophilic molecule conjugate provides a method for delivering a photodynamic therapeutic agent to a desired site with a high concentration of oxygen. By presenting the agent in this way, it is expected that a patient will experience less toxicity.

19 Claims, No Drawings

OTHER PUBLICATIONS

Sessler et al., "Expanded Porphyrins: The Synthesis and Metal Binding Properties of Novel Tripyrrane–Containing Macrocycles", *J. Coord. Chem.*, 18:99–104, 1988.

Sessler et al., "The Synthesis and Structure of a Novel 22 π–Electron Aromatic Pentadentate Macrocyclic Ligand: An Expanded Porphyrin", Toronto ACS Meeting, Jun. 1988. USA.

Sessler et al., "A Water–Stable Gadolinium (III) Complex Derived from a New Pentadentate "Expanded Porphyrin" Ligand", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived ("Texaphyrin"–type) Macrocycles: Potential Photosensitizers Which Absorb in the Far–red Spectral Region", *SPIE, Optical Methods for Tumor Treatment and Early Diagnosis: Mechanism and Technique*, 1426:318–329, 1991.

Sessler et al., "Texaphyrin': A Novel 22 π–Electron Aromatic Pentadentate Macrocyclic Ligand", *ACS meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide(III) Texaphyrins," *Inorganic Chemistry*, 32(14):3175–3187, 1993.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Paper*, Part 1, 204th ACS National Meeting, Aug. 23–28, 1992, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, α 22 π –Electron "Expanded Porphyrin": Possible Approaches to Prophylactic Blood Purification Protocols," *SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Sessler et al., "Texaphyrins: Synthesis and Applications," *Accounts of Chemical Research*, 27(2):43–50, 1994.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

Furuta et al., "Enhanced Transport of Nucleosides and Nucleoside Analogues with Complementary Base–Pairing Agents," *Journal of the American Chemical Society*, 113:4706–4707, 1991.

Sessler et al., "Anion Binding: A New Direction In Porphyrin–Related Research," *Pure & Applied Chem.*, 65(3):393–398, 1993.

Sessler et al., "Synthesis and Binding Properties of Monomeric and Dimeric Guanine and Cytosine Amine Derivatives," *J. Org. Chem.*, 1992, 57:818–826.

T.D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler et al., "Gadolinium (III) Texaphyrin: A Novel MRI Contrast Agent," *Journal of the American Chemical Society*, 115(22):10368–10369, 1993.

Iverson et al., "Interactions Between Expanded Porphyrins and Nucleic Acids," *Pure Applied Chemistry*, 66(4):845–850, 1994.

Magda et al., "Site–Specific Hydrolysis of RNA by Europium (III) Texaphyrin Conjugated to a Synthetic Oligodeoxyribonucleotide," *Journal of the American Chemical Society*, 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

Mastruzzo et al., "Targeted Photochemical Modification of HIV–Derived Oligoribonucleotides by Antisense Oligodeoxynucleotides Linked to Porphyrins,"*Photochemistry and Photobiology*, vol. 60, No. 4, pp. 316–322, 1994.

Dougherty, "Photosensitizers: Therapy and Detection of Malignant Tumors", *Photochem. Photobiol.*, 45:879–889, (1987).

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates, in Transition Metals in Supramolecular Chemistry," L. Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 1994.

International Search Report mailed Feb. 22, 1994.

International Search Report mailed Feb. 3, 1994.

Ehrenberg et al., "Spectroscopy, Photokinetics and Cellular Effect of Far–Red and Near Infrared Absorbing Photosensitizers," *Proc. SPIE–Int. Soc. Opt. Eng 1992*, 1645 (Proc. Opt. Methods Tumor Treat. Dect.: Mech. Tech. Photodyn. Ther.., 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.

Lasic et al., "Liposomes Revisited," *Science*, vol. 267, pp. 1275–1276, Mar. 3, 1995.

Brown and Truscott, "New Light on Cancer Therapy," *Chemistry in Britain*, 955–958, 1993.

Ehrenberg et al., "The Binding and Photosensitization Effects of Tetrabenzoporphyrins and Texaphyrin in Bacterial Cells," *Lasers in Medical Science*, 8:197–203, 1993.

Morgan and Skalkos, "Second Generation Sensitizers: Where are We and Where Should We Be Going?" *Proc. SPIE Int. Soc. Opt. Eng. Ser.*, 6:87–106, 1990.

Horstman, "Study to examine skin cancer drug activated by light," *Stanford University Campus Report*, Mar., 1996.

Biolo, et al., "Photodynamic Therapy of B16 Pigmented Melanoma With Liposome–Delivered Si(IV)–Naphthalocyanine," *Photochemistry and Photobiology*, vol. 59, No. 3, pp. 362–265, 1994.

Haylett, et al., "Pharmacokinetic and therapeutic outcome in melanoma cells, of the administration of symmetric and asymmetric cationic photosensitizers," *Cancer Letters 88*, pp. 191–199, 1995.

Leunig, et al., "Tumour localisation kinetics of photofrin and three synthetic porphyrinoids in an amelanotic melanoma of the hamster," *Br. J. Cancer*, 68, pp. 225–234, 1993.

Nelson, et al., "Photodynamic Therapy of Human Malignant Melanoma Xenografts in Athymic Nude Mice," *Journal of the National Cancer Institute*, vol. 80, No. 1, Mar. 2, 1988.

Sealy, et al., "Photosensitization of Melanin: An Electron Spin Resonance Study of Sensitized Radical Production and Oxygen Consumption," *Photochemistry and Photobiology*, vol. 40, No. 4, pp. 453–459, 1984.

PCT/US90/01208 Int'l Search Report mailed Aug. 2, 1990.

PCT/US95/12312 International Search Report mailed Feb. 9, 1996.

König et al., "Photodynamic Activity of Liposome–Delivered Cd–Texaphyrin Using Tumor–Bearing Nude Mice", *Lasers in Surgery and Medicine* 13:522–527, 1993.

Pharmacyclics' Press Release, "Pharmacyclics Expands Photodynamic Therapy Trial to Stanford," Mar. 28, 1996.

Schenning A P H J et al: "An Amphiphilic Porphyrin with Unexpected Aggregation Behaviour," *Tetrahedron Letters*, 34:44;7077–7080 Oct. 1993.

Search Report for PCT/US97/09501 mailed Feb. 4, 1998.

Monsigny, et al., "Glycoconjugates as carriers for specific delivery of therapeutic drugs and genes." *ADV. Drug Delivery. Rev* (Netherlands), 1994 (Abstract).

Pharmacyclics Press Release, "Pharmacyclics Initiates Phase Ib/II Trial of GD–Tex for Use in Treatment of Cancer Patients Receiving Radiation Therapy," Sunnyvale, California, Jan. 29, 1996.

Pharmacyclics–Lutetium Texaphyrin Background (Mar. 27, 1996).

Pharmacyclics Press Release, "Pharmacyclics' Photodynamic Therapy Agent Lu–Tex is Well Tolerated and Demonstrates Activity in a Multicenter Phase I Cancer Trial," Sunnyvale, California, Jun. 17, 1996.

Pharmacyclics F–D–C Reports–The Pink Sheet "Pharmacyclics Gd–Tex for brain Metastases in Phase I/II multicenter trial", Jul. 1, 1996; vol. 58, Issue 27.

Pharmacyclics Press Release, "Pharmacyclics, Hoechst Celanese Forge Manufacturing Pact for Photodynamic Therapy and Radiation Sensitizer Products," Sunnyvale, California, Sep. 12, 1996.

Pharmacyclics Press Release, "Pharmacyclics Completes Phase I Lu–Tex Trials in Photodynamic Cancer Treatment," Sunnyvale, California, Jan. 7, 1997.

Pharmacyclics Press Release, "Pharmacyclics Announce NCI Decision Network Approval to Collaborate on Two Anti–Cancer Compounds," Sunnyvale, California, Mar. 11, 1997.

Pharmacyclics Press Release, "Pharmacyclics Presents Results and Updates Status for Photodynamic Therapy Agent at ASCO Meeting," Sunnyvale, California, May 19, 1997.

Pharmacyclics Press Release, "Pharmacyclics Announces Interim Results of GD–Tex," Sunnyvale, California, May 20, 1997.

Pharmacyclics Press Release, "NCI to Sponsor 9 Clinical Studies With Pharmacyclics' GD–Tex", Sunnyvale, California, Sep. 16, 1997.

Pharmacyclics Press Release, "Pharmacyclics Completes Dose Esclation Portion of Phase Ib/II Clinical Trial With Radiation Sensitizer", Sunnyvale, California, Sep. 30, 1997.

Pharmacyclics Press Release, "Pharmacyclics Presents Interim Safety and Efficacy Data of Radiation Sensitizer at American Society for Therapeutic Radiology and Oncology Meeting" Sunnyvale, California, Oct. 20, 1997.

Pharmacyclics Press Release, "Pharmacyclics Announces Licensing Agreement with Nycomed for Cancer Photosensitizer", Sunnyvale, California, Oct. 20, 1997.

Pharmacyclics Press Release, "Pharmacyclics Signs Ophthalmology Deal With Alcon for Photosensitizer", Sunnyvale, California, Dec. 17, 1997.

Pharmacyclics Press Release, Pharmacyclics Completes Patient Enrollment in Phase II GD–Tex Clinial Trial, Mar. 10, 1998.

Renschler, et al., Photodynamic therapy trials with Luteium Texaphyrin PCI–0123, MPM–F5 *Abstract of the 25$^{th}$ Annual Meeting of the American Society for Photobiology*, May 1997 (Abstract).

Woodburn, K. and David Kessel, "Effect of Density–Gradients on the Binding of Photosensitizing Agents to Plasma Proteins," *Int. J. Biochem. Cell Biol.*, vol. 27, No. 5, pp. 499–506, 1995.

Woodburn, et al., "Localization and Efficacy Analysis of the Phototherapeutic Lutetium Texaphyrin (PCI–0123) in the Murine EMT6 Sarcoma Model," *Photochemistry and Photobiology*, 65(3):410–415, 1997.

Woodburn, et al., "Photoangioplasty Following Intravenous Lutetium Texaphyrin: A Far Red, Light Activated Photodynamic Therapy Agent that Selectively Accumulates in Atheroma."(Abstract) Oct. 21, 1997.

Woodburn, et al., "Biological Analysis of Lutetium Texaphyrin (PCI–0123)."date unknown , Abstract of the 24$^{th}$ Annual Meeting of the American Society for Photobiology.

Young, et al., "Preclinical Evaluation of Gadolinium (III) Texaphyrin Complex–A New Paramagnetic Contrast Agent for Magnetic Resonance Imaging", *Investigative Radiology*, 29(3):330–338, 1994.

Young, et al., "Lutetium Texaphyrin (PCI–0123): A Near–Infrared, Water–Soluble Photosensitizer," *Photochemistry and Photobiology*, 63(6):892–897, 1996.

Sessler et al., "Texaphyrin", one–page, date unknown.

* cited by examiner

MEMBRANE INCORPORATION OF TEXAPHYRINS

This application is a continuation application of copending international application PCT/US97/09501 filed Jun. 4, 1997, which claims priority to converted provisional application No. 60/056,917, (formerly U.S. Ser. No. 08/657,947), filed Jun. 4, 1996, now abandoned. The patent applications are incorporated by reference herein.

BACKGROUND OF THE INVENTION

A drug delivery system should deliver drug at a rate dictated by the needs of a medical procedure over the period of the procedure, that is, the goal of any drug delivery system is to provide a therapeutic amount of drug to the proper site in the body to promptly achieve, and then maintain, the desired drug concentration. This objective emphasizes the need for spatial placement and temporal delivery of a drug or treatment. Spatial placement is the targeting of a drug to a specific organ, tissue, or bodily system such as the blood stream; while temporal delivery refers to controlling the rate of drug delivery to the target.

Targeted drug delivery systems include colloidal drug delivery systems and resealed or modified cells, for example, resealed or modified erythrocytes or leukocytes. Colloidal drug delivery systems include nanoparticles, microcapsules, nanocapsules, macromolecular complexes, polymeric beads, microspheres, liposomes, and lipid vesicles.

Liposomes are formed from phospholipids that are dispersed in an aqueous medium and spontaneously form multilamellar concentric bilayer vesicles (also termed multilamellar vesicles (MLVs)). MLVs generally have diameters of from 4 mm to 25 nm. Sonication or solvent dilution of MLVs results in the formation of small unilamellar vesicles (SUVs) with diameters in the range of 300 to 500 Å.

Liposomes resemble cellular membranes, and water- or lipid-soluble substances can be entrapped in the aqueous spaces or within the bilayer, respectively. An important determinant in entrapping compounds is the physicochemical properties of the compound itself. Polar compounds are trapped in the aqueous spaces and are released through permeation or when the bilayer is broken; nonpolar compounds bind to the lipid bilayer of the vesicle, and tend to remain there unless the bilayer is disrupted by temperature or exposure to lipoproteins.

Liposomes may interact with cells via a number of different mechanisms, for example: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; or by transfer of liposomal lipids to cellular or subcellular membranes, or vice versa, without any association of the liposome contents. It often is difficult to determine which mechanism is operative and more than one may operate at the same time.

Intravenously injected liposomes may persist in tissues for hours or days, depending on their composition, and half-lives in the blood range from minutes to several hours. Larger liposomes are taken up rapidly by phagocytic cells of the reticuloendothelial system and exit only in places where large openings or pores exist in the capillary endothelium, such as the sinusoids of the liver or spleen. Thus, these organs are the predominant site of uptake. On the other hand, smaller liposomes show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Attempts to overcome the limitation on targeting of liposomes have centered around two approaches. One is the use of antibodies, bound to the liposome surface, to direct the antibody and the liposome contents to specific antigenic receptors located on a particular cell-type surface. Further, carbohydrate determinants (glycoprotein or glycolipid cell-surface components that play a role in cell-cell recognition, interaction and adhesion) may also be used as recognition sites since they have potential in directing liposomes to particular cell types.

Further lipid vesicles, such as nonphospholipid paucilamellar lipid vesicles (PLV's), are made from materials such as polyoxyethylene fatty esters, polyoxyethylene fatty acid ethers, diethanolamines, long-chain acyl amino acid amides, long-chain acyl amides, polyoxyethylene sorbitan mono and tristearates and oleates, polyoxyethylene glyceryl monostearates and monooleates, and glyceryl monostearates and monooleates, (U.S. Pat. Nos. 4,911,928, 4,917,951, and 5,000,960).

Resealed erythrocytes are another form of targeted drug delivery. When erythrocytes are suspended in a hypotonic medium, they swell to about one and a half times their normal size, and the membrane weakens, resulting in the formation of small pores. The pores allow equilibration of the intracellular and extracellular solutions. If the ionic strength of the medium then is adjusted to isotonicity, the pores will close and cause the membrane of the erythrocyte to return to normal or "reseal". Using this technique with a drug present in the extracellular solution, it is possible to entrap a substantial amount of the drug inside the resealed erythrocyte and to use this system for targeted delivery via intravenous injection.

Studies on the behavior of normal and modified reinfused erythrocytes indicate that, in general, normal aging erythrocytes, slightly damaged erythrocytes and those coated lightly with antibodies are sequestered in the spleen after intravenous reinfusion; but heavily damaged or modified erythrocytes are removed from the circulation by the liver. This suggests that resealed erythrocytes can be targeted selectively to either the liver or spleen, which can be viewed as a disadvantage in that other organs and tissues are inaccessible. Thus, the application of this system to targeted delivery has been limited mainly to treatment of lysosomal storage diseases and metal toxicity, where the site of drug action is in the reticuloendothelial system.

Labeling of red blood cells with chromium-51 and white blood cells with indium-111, as well as labeling of liposomes with contrast media and therapeutic agents is known. U.S. Pat. No. 5,466,438 relates to liposoluble complexes of paramagnetic ions and compounds bearing long acyl chains useful as magnetic resonance imaging contrast agents. U.S. Pat. No. 5,000,960 relates to coupling a molecule having a free sulfhydryl group to a lipid vesicle having a free sulfhydryl group incorporated as one of the structural molecules of the lipid phase thereby forming a covalent disulfide bond linkage. U.S. Pat. No. 4,931,276 relates to methods for introducing desired agents into red blood cells, and U.S. Pat. No. 4,478,824 relates to methods and apparatus for causing reversible intracellular hypertonicity in red blood cells of mammals in order to introduce desired materials into the cells, or achieve therapeutically desirable changes in the characteristics of intracellular hemoglobin. Further, poor accumulation of liposomal cadmium-texaphyrin in tumor tissue was cited as a possible explanation for low efficiency of photodynaric therapy in König et al., (*Lasers in Surgery and Medicine* 13:522, 1993; in: Photodynamic Therapy and Biomedical Lasers, P. Spinelli, M. Dal Fante and R. Marchesini, eds., Elsevier Science Publishers, 1992, 802).

Photodynamic therapy (PDT) is a treatment technique that uses a photosensitizing dye that produces cytotoxic materials, such as singlet oxygen ($O_2(^1D_g)$) from benign precursors (e.g. (($O_2(^3S_g-)$)), when irradiated in the presence of oxygen. Other reactive species such as superoxide, hydroperoxyl, or hydroxyl radicals may be involved. At the doses used, neither the light nor the drug has any independent activity against the disease target.

The effectiveness of PDT is predicated on three main factors: i) The photosensitive dyes used in PDT preferably have the ability to localize at the treatment site as opposed to surrounding tissue. ii) The high reactivity and short lifetime of activated oxygen means that it has a very short range and is unlikely to escape from the cell in which it is produced; cytotoxicity is therefore restricted to the precise region of photoactivated drug. iii) Developments in light delivery, such as lasers, light emitting diodes, and fiber optics, allow a beam of intense light to be delivered accurately to many parts of the body.

In recent years, considerable effort has been devoted to the synthesis and study of new photosensitizers (a review is found in Brown, S. B. and Truscott, T. G., 1993, *Chemistry in Britain*, 955–958). The development of more effective photochemotherapeutic agents requires the synthesis of compounds which absorb in the spectral region where living tissues are relatively transparent (i.e., 700–1000 nm), have high triplet quantum yields, are minimally toxic, and have physiologically acceptable water/lipid partition coefficients. Texaphyrins have proven to be effective sensitizers for generating singlet oxygen and for photodynamic therapy (U.S. Pat. Nos. 5,272,142; 5,292,414; 5,439,570; and 5,451,576, incorporated by reference herein).

Magnetic resonance imaging has become an important diagnostic tool in medicine, especially for tumor imaging. Imaging of tissue is dependent upon a difference in the relaxation rates of nuclear spins of water protons from various tissues in a magnetic field. The relaxation rate can be enhanced by use of a contrast agent, thereby improving a resulting image. The gadolinium cation is a superior contrast agent due to its seven unpaired f-electrons and high magnetic moment. However, gadolinium cation is too toxic to be used directly for imaging at concentrations required for effective enhancement. Texaphyrins bind the gadolinium ion in a stable manner and have proved to be nontoxic and effective contrast agents for imaging (U.S. Pat. Nos. 5,252,720, 5,451,576, and 5,256,399, incorporated by reference herein). Further development of texaphyrin-based magnetic resonance imaging protocols would be of significant value for the improvement of medical diagnostic imaging.

Macular degeneration due to damage or breakdown of the macula, underlying tissue, or adjacent tissue is the leading cause of decreased visual acuity and impairment of reading and fine "close-up" vision. Age-related macular degeneration (ARMD) is the major cause of severe visual loss in the elderly. The most common form of macular degeneration is called "dry" or involutional macular degeneration and results from the thinning of vascular and other structural or nutritional tissues underlying the retina in the macular region. A more severe form is termed "wet" or exudative macular degeneration. In this form, blood vessels in the choroidal layer (a layer underneath the retina and providing nourishment to the retina) break through a thin protective layer between the two tissues. These blood vessels may grow abnormally directly beneath the retina in a rapid uncontrolled fashion; resulting in oozing, bleeding, or eventually scar tissue formation in the macula which leads to severe loss of central vision. This process is termed choroidal neovascularization.

Neovascularization results in visual loss in other eye diseases including neovascular glaucoma, ocular histoplasmosis syndrome, myopia, diabetes, pterygium, and infectious and inflammatory diseases. In histoplasmosis syndrome, a series of events occur in the choroidal layer of the inside lining of the back of the eye resulting in localized inflammation of the choroid and consequent scarring with loss of function of the involved retina and production of a blind spot (scotoma). In some cases, the choroid layer is provoked to produce new blood vessels that are much more fragile than normal blood vessels. They have a tendency to bleed with additional scarring, and loss of function of the overlying retina. Diabetic retinopathy involves retinal rather than choroidal blood vessels resulting in hemorrhages, vascular irregularities, and whitish exudates. Retinal neovascularization may occur in the most severe forms.

Current diagnosis of ocular disorders often includes use of a fluorescein or indocyanine green angiogram. In this procedure, the dye is injected into the blood stream through a vein in the arm. Special filters are placed in the light path, and in front of the film, to permit only the fluorescent dye to be seen as it passes through the vessels in the retina Pictures of the vascular anatomy are taken of the retina and macula as the dye passes through the blood vessels of the back of the eye. Vascular occlusions or leakage of dye indicates abnormal vasculature. Optical coherence tomography is another technique that uses noncontact imaging and provides high-depth resolution in cross-sectional tomographs of the retina.

Current treatment of neovascularization relies on ablation of blood vessels using laser photocoagulation. However, such treatment requires thermal destruction of the tissue, and is accompanied by full-thickness retinal damage, as well as damage to medium and large choroidal vessels. Further, the patient is left with an atrophic scar and visual scotoma. Moreover, recurrences are common, and the prognosis for the patient's condition is poor.

Developing strategies, such as PDT, have sought more selective closure of the blood vessels to preserve the overlying neurosensory retina PDT of conditions in the eye characterized by neovascularization has been attempted using the conventional porphyrin derivatives such as hematoporphyrin derivative and PHOTOFRIN® porfimer sodium. Problems have been encountered in this context due to interference from eye pigments. In addition, phthalocyanine and benzoporphyrin derivatives have been used in photodynamic treatment. PCT publication WO 95 24930 and Miller et al., (*Archives of Ophthalmology*, June, 1995) relate to treatment of eye conditions characterized by unwanted neovasculature comprising administering a green porphyrin to the neovasculature and irradiating the neovasculature with light having a wavelength of 550–695 nm. U.S. Pat. No. 5,166,197 relates to phthalocyanine derivatives reportedly useful for macular degeneration. Asrani and Zeimer (*British Journal of Ophthalmology*, 1995, 79:766–770) relate to photoocclusion of ocular vessels using a phthalocyanine encapsulated in heat-sensitive liposomes. Levy (*Semin. Oncol.* 1994, 21/6, suppl. 15 (4–10)) relates to photodynamic therapy and macular degeneration with porfimer sodium (PHOTOFRIN®, requiring light of 630 nm and causing cutaneous photosensitivity that may last for up to 6 weeks), and benzoporphyrin derivative (BPD verteporfin, causing cutaneous photosensitivity of a few days). Lin et al. relate to the photodynamic occlusion of choroidal vessels using benzoporphyrin derivative BPD-MA. Further, BPD and tin purpurin (SnET2) are insoluble in aqueous solutions and require hydrophobic vehicles for administration.

Texaphyrins are aromatic pentadentate macrocyclic expanded porphyrins" useful as MRI contrast agents, as radiosensitizers and in photodynamic therapy. Texaphyrin is considered as being an aromatic benzannulene containing both 18- and 22-electron delocalization pathways. Texaphyrin molecules absorb strongly in the tissue-transparent 700–900 nm range, and they exhibit inherent selective uptake or biolocalization in certain tissues, particularly regions such as, for example, liver, atheroma or tumor tissue. Paramagnetic texaphyrins have exhibited significant tumor selectivity as detected by magnetic resonance imaging. Texaphyrins and water-soluble texaphyrins, method of preparation and various uses have been described in U.S. Pat. Nos. 4,935,498; 5,162,509; 5,252,720; 5,256,399; 5,272,142; 5,292,414; 5,369,101; 5,432,171; 5,439,570; 5,451,576; 5,457,183; 5,475,104 5,504,205; 5,525,325; 5,559,207; 5,565,552; 5,567,687; 5,569,759; 5,580,543; 5,583,220; 5,587,371; 5,587,463; 5,591,422; 5,594,136; 5,595,726; 5,599,923; 5,599,928; 5,601,802; 5,607,924; and 5,622,946; PCT publications WO 90/10633, 94/29316, 95/10307, 95/21845, and 96/09315; allowed U.S. patent application Ser. Nos. 08/484,551 and 08/624,311; and pending U.S. patent application Ser. Nos. 08/458,347; 08/657, 947; 08/591,318; 08/700,277; and 08/763,451; each patent, publication, and application is incorporated herein by reference.

Problems with prior art drug and PDT delivery systems include lack of specificity, toxicity, expense, and technical difficulties, among others. Problems with prior art magnetic resonance imaging contrast agents include insufficient differential biolocalization, insufficient signal, toxicity, and slow clearance, among others. Because of these problems, known procedures are not completely satisfactory, and the present inventors have searched for improvements.

SUMMARY OF THE INVENTION

The present invention relates generally to the fields of targeted drug delivery, medical imaging, diagnosis, and treatment. More particularly, it concerns compositions having a texaphyrin-hpophilic molecule conjugate loaded into a biological vesicle; and methods for imaging, diagnosis and treatment using this loaded vesicle.

Accordingly, the present invention provides compositions comprising a texaphyrin-lipophilic molecule-vesicle complex. Such compositions include cells of the vascular system, such as red blood cells or white blood cells, and micellar vesicles such as liposomes or nonphospholipid vesicles, loaded with a texaphyrin conjugated to a lipophiliz molecule. When the texaphyrin portion of the complex is photosensitive and when the complex is irradiated, the complex ruptures, depositing its contents. The invention therefore includes methods for delivering diagnostic or therapeutic agents via loaded texaphyrin-lipophilic molecule-vesicle complexes.

"Loading" means labeling of membranes of a vesicle, embedding into a vesicular membrane, or incorporation into the interior of a vesicle. In particular, loading would include attachment to or within cells circulating within the vascular system or to or within liposomes or other lipid vesicles.

A texaphyrin-lipophilic molecule-biological vesicle complex is an embodiment of the present invention. By "biological vesicle" is meant a membranous structure having a lipid bilayer, or a micelle. By "lipid bilayer" is meant a bimolecular sheet of phospholipids and/or glycolipids. A biological vesicle may be a cell, such as a red cell or white cell, or membranous fragment thereof; a liposomal membrane; a nonphospholipid vesicle, or a colloidal drug delivery system. In one embodiment of the present invention, the biological vesicle is a resealed red blood cell.

As used herein, a "lipophilic molecule" is a molecule having a lipid-water distribution coefficient that is optimal for localization to lipid-rich tissues or materials compared to localization in surrounding nonlipid-rich tissues or materials. "Lipid-rich" means having a greater amount of triglyceride, cholesterol, fatty acids or the like. Lipophilic molecules that may be conjugated to a texaphyrin include cholesterol; steroids including progestagens such as progesterone, glucocorticoids such as cortisol, mineralocorticoids such as aldosterone, androgens such as testosterone and androstenedione, and estrogens such as estrone and estradiol; phospholipids such as phosphatidyl choline, phosphatidyl serine, phosphatidyl ethanolamine, phosphatidyl inositol, or cardiolipin; sphingolipids such as sphingomyelin; glycolipids such as cerebroside, or ganglioside; molecules having isoprenoid side chains such as vitamin $K_2$, coenzyme $Q_{10}$, chlorophyll, or carotenoids; low density lipoprotein (LDL); or the like. Preferred lipophilic molecules are steroids, more preferably estradiol, or cholesterol, for example.

A method for photodynamic therapy is also an aspect of the present invention. The method comprises administering a photosensitive texaphyrin-lipophilic molecule-vesicle complex to a subject, and irradiating the complex. Preferably, the vesicle portion of the complex is a red blood cell, and in one embodiment, the subject is a donor of the red blood cell.

When loaded with a photosensitive texaphyrin-lipophilic molecule conjugate, a loaded vesicle has utility as a diagnostic or therapeutic agent since the cell or liposome can be disrupted using an appropriate light source, thereby depositing a diagnostic or therapeutic agent in vivo. Therefore, a method for delivery of an agent to a targeted biological site is a further embodiment of the present invention. The method comprises i) loading a vesicle with a photosensitive texaphyrin-lipophilic molecule conjugate and the agent to form a complex; ii) allowing the complex to locate at the targeted biological site; and iii) irradiating the complex. The complex is lysed by irradiating, thereby delivering the agent to the targeted biological site. The agent may be a diagnostic agent, photodynamic therapy agent, a chemotherapeutic agent, a radiation sensitizing agent, or naturally occurring cellular contents of a cell. A preferred vesicle portion of a complex to be loaded is a red blood cell, a preferred lipophilic molecule portion of a complex is estradiol or cholesterol, and the photosensitive texaphyrin-lipophilic molecule conjugate may have a diamagnetic metal cation bound by the texaphyrin. A preferred diamagnetic metal cation is Lu(III), La(III), In(III), Y(III), Zn(II) or Cd(II); a most preferred diamagnetic metal cation is Lu(III). Availability of red blood cells loaded with a photosensitive texaphyrin-lipophilic molecule conjugate provides a method for delivering a therapeutic PDT agent to a desired site with a high concentration of oxygen. By presenting a PDT agent this way, it is expected that the patient will experience less toxicity.

The method of photolysis of loaded blood cells or liposomes involves at least two sources of specificity. A first source of specificity is the natural localization of loaded cells or liposomes into the blood, liver, spleen, bone marrow, or lymphoid organs. A second source of specificity is the positioning of the laser light. Such positioning of laser light, either by manual or mechanical means, would be particularly advantageous when the photolysis is to be effected at a particular biological locus, such as, for instance, a deep-seated tumor site. Here, the fact that the-texaphyrins absorb light at wavelengths where bodily tissues are relatively transparent (700–900 nm) is particularly advantageous. This procedure allows for the effective implementation of light-based strategies at loci deep within the body with relatively little deleterious light-based photosensitization of other tissues where the texaphyrin conjugates are not localized or where the light is not focused.

Further, the present invention provides for the possibility of using the patient's own blood for loading with a diagnostic or a therapeutic agent and a texaphyrin-lipophilic molecule conjugate. In so doing, a uniquely "customized" therapy with reduced toxicity, increased circulation, and maximum therapeutic effect is provided.

Vesicles loaded with a photosensitive texaphyrin-lipophilic molecule conjugate and a chemotherapeutic drug have utility in conventional chemotherapy. In such a case, by directing laser light at a tumor and lysing the vesicle, a chemotherapeutic agent is released only in proximity to the cancer. In addition, a localized photodynamic therapeutic effect of irradiating the texaphyrin will occur.

Another embodiment of the present invention is a method of imaging. The method comprises the steps of administering a detectable texaphyrin-lipophilic molecule-vesicle complex to a subject, and imaging the complex.

When the detectable texaphyrin is fluorescent, imaging is by observing fluorescence of the texaphyrin. When the detectable texaphyrin is complexed with a paramagnetic metal cation, imaging is by magnetic resonance imaging. Further imaging methods include x-ray imaging, Raman scattering, magnetometry (bioluminescence), or gamma scanning when the texaphyrin is complexed with a gamma emitting isotope. For fluorescent imaging, texaphyrins may be activated by 400–500 nm light (the Soret band) or 700–900 nm light, preferably 700–800 nm, (the Q band) and, therefore, provide considerable versatility for use in humans.

The term "fluorescent", as used herein, means that upon photoirradiation by light associated with the absorption profile of texaphyrin, light is emitted at a longer wavelength by the irradiated texaphyrin. All texaphyrins are fluorescent, albeit, to varying degrees, and texaphyrins complexed with Y(III), Lu(III), Gd(III), Dy(III), Eu(III), or Mn(III) are particularly preferred as fluorescent texaphyrins, for example.

In addition to fluorescent detection, texaphyrins may be imaged by x-radiation, by Raman scattering, or by magnetometry; further, texaphyrins complexed with a paramagnetic metal cation may be used for magnetic resonance imaging. Preferred paramagnetic metal cations for complexing with a texaphyrin include Mn(III), Mn(III), Fe(III), or trivalent lanthanide metals other than La(III), Lu(III), and Pm(III). More preferably, the paramagnetic metal is Mn(II), Mn(M), Dy(III), or Gd(III); most preferably, Gd(III). Any of various types of magnetic resonance imaging can be employed in the practice of the invention, including, for example, nuclear magnetic resonance (NMR), NMR spectroscopy, and electronic spin resonance (ESR). The preferred imaging technique is NMR.

Gamma particle detection may be used to image a texaphyrin complexed to a gamma-emitting metal. $^{51}$Chromium, $^{68}$gallium, $^{99}$technetium, or $^{111}$indium are preferred metals for complexing to texaphyrins for gamma particle scanning. Monochromatic X-ray photon sources may be used for imaging also.

The present invention is useful in imaging a patient generally, and/or in specifically diagnosing the presence of diseased tissue in a patient. The imaging process of the present invention may be carried out by administering a detectable texaphyrin-lipophilic molecule-vesicle complex of the invention to a patient, and then scanning the patient to obtain visible images of an internal region of a patient and/or of any diseased tissue in that region. The complexes of the present invention are particularly useful in providing images of the blood pool, liver, reticuloendothelial system, spleen, bone marrow, lymph nodes, and muscle; they are especially effective blood pool agents, and are highly effective at enhancing the liver and highly useful for improving the detection of hepatic metastases. Red blood cells loaded with a texaphyrin-lipophilic molecule conjugate, when injected intravenously, have been demonstrated to serve as a contrast agent for MRI Vesicles loaded with a paramagnetic texaphyrin-lipophilic molecule conjugate have utility as a blood pool contrast agent, facilitating the enhancement of normal tissues, magnetic resonance angiography, and marking areas of damaged endothelium by their egress through fenestrations or damaged portions of the blood vascular system. The patient may be any type of animal, but preferably is a mammal, and most preferably is a human.

Texaphyrin-lipophilic molecule conjugates and texaphyrin-lipophilic molecule-vesicle complexes are also provided for use in ocular diagnosis and therapy, in particular, therapy involving photodynamic therapy of conditions of the eye characterized by abnormal vasculature. Accordingly, an aspect of the present invention is directed to a method for carrying out angiography of the eye, i.e., observing, vasculature of an eye of a subjecl The method comprises the steps of administering a detectable texaphyrin-lipophilic molecule or texaphyrin-lipophilic molecule-vesicle complex to the subject; and observing the vasculature of the eye. Observing may be by fluorescence or other imaging methods as herein described.

In a further aspect of the invention, a method for treating an ocular condition of a subject characterized by abnormal vasculature is provided. The method comprises the steps of administering a photosensitive texaphyrin-lipophilic molecule conjugate or a photosensitive texaphyrin-lipophilic molecule-vesicle complex to the subject; and photoirradiating the vasculature. The method may further comprise the step of observing the ocular condition of the subject by imaging the texaphyrin as stated herein.

A method for photodynamic therapy of macular degeneration of a subject, comprising the steps of administering a photosensitive texaphyrin-lipophilic molecule conjugate or texaphyrin-lipophilic molecule-vesicle complex to the subject; and photoirradiating the macula is another aspect of the invention.

A method for observing and treating an ocular condition of a subject characterized by abnormal vasculature using a single agent is also an aspect of the invention. The method comprises the steps of administering a photosensitive fluorescent texaphyrin-lipophilic molecule or a photosensitive fluorescent texaphyrin-lipophilic molecule-vesicle complex to the subject; observing the ocular condition of the subject by fluorescence of the texaphyrin; and photoirradiating the vasculature.

For angiography, texaphyrins may be activated by 400–500 nm light (the Soret band) or 700–800 nm light (the Q band) and, therefore, provide considerable versatility for use in humans. For phototherapy, texaphyrins may be irradiated at 400–500 nm and at longer wavelengths of light where ocular tissues are relatively transparent, especially where light can penetrate blood and vascular tissue, i.e., 700–800 nm, especially at about 732 nm. Texaphyrins are particularly effective as visualizing agents in angiography of ocular blood vessels due to their localization in areas of abnormal permeability or damage as described in U.S. Ser. No. 08/763,451, incorporated by reference herein.

Texaphyrin-lipophilic molecules or texaphyrin-lipophilic molecule-vesicle complexes can be administered in a bolus injection allowing for a sufficiently large amount of drug to be present in the blood and for fast-turnaround between dosing and treatment. Further, texaphyrins are cleared quickly from the body; no toxicity to the eye has been observed in the use of texaphyrins in angiography.

A method of inducing formation of antibodies having binding specificity for a texaphyrin in a subject is also an aspect of the present invention. This method comprises administering a photosensitive texaphyrin-lipophilic molecule-vesicle complex to a subject, and irradiating the complex. Irradiating with light disrupts the vesicle, causing the contents to be deposited in the subject, thereby exposing the subject to the texaphyrin and inducing antibody production to texaphyrin. In this case, the texaphyrin may be considered a hapten; if the vesicle is a foreign cell, then the vesicle may be considered an adjuvant in addition to being the carrier that delivers the texaphyrin. By "foreign" is meant that the loaded vesicle is from a different species of animal than the animal into which the loaded cell is administered. For example, the cell for loading may be a goat cell, and the subject administered the loaded cell may be a rabbit.

In addition, a further immunogen may be loaded into the vesicle for inducing antibodies having binding specificity for that immunogen. Antibodies having binding specificity for the cellular contents of the disrupted cell may also be formed.

A further aspect of the invention is an antibody having binding specificity for a texaphyrin molecule. Such antibodies are useful for purification of a texaphyrin, for screening assays for the presence of a texaphyrin, or for the presence of texaphyrin degradation products from metabolic processes.

A method of making a texaphyrin-lipophilic molecule-cell complex is an aspect of the present invention. The method comprises i) obtaining a texaphyrin-lipophilic molecule conjugate, and ii) incubating a cell with the texaphyrin-lipophilic molecule conjugate in a hypotonic saline solution for a time and under conditions wherein a texaphyrin-lipophilic molecule-cell complex is formed An optional step is to include a drug or therapeutic agent when incubating in the hypotonic solution. A preferred cell is an erythrocyte. Advantages of using resealed or modified autologous erythrocytes as drug carriers include the fact that they are biodegradable, fully biocompatible, and nonimmunogenic; they exhibit flexibility in circulation time depending on their physicochemical properties; the entrapped drug is shielded from immunologic detection; and chemical modification of a drug is not required.

A method of making a texaphyrin-lipophilic molecule-liposome complex is an aspect of the present invention. The method comprises the step of incubating a texaphyrin-lipophilic molecule conjugate with a lipid or incorporating a texaphyrin-lipophilic molecule into a preformed liposome or micelle for a time and under conditions wherein a texaphyrin-lipophilic molecule-liposome complex is formed. An optional step is to include a drug or therapeutic agent during the incubation or incorporation.

In summary, a vesicle loaded with a texaphyrin-lipophilic molecule conjugate is useful in medical imaging, diagnosis, and therapy.

Following long-standing patent law convention, the terms "a" and "an" mean "one or more" when used in this application, including the claims.

DETAILED DESCRIPTION OF THE PREFERRED EMBODIMENTS

Loading of a biological vesicle, such as a red blood cell (RBC), white blood cell (WBC), or a liposome with a texaphyrin-lipophilic molecule conjugate has previously not been shown. In the present invention, RBC's were successfully loaded with GdT2BET-estradiol conjugate (GTE $1_A$). However, attempted loading with GdT2BET alone was not successful, thereby indicating that a lipophilic molecule "handle" is an important aspect of the texaphyrin conjugate for loading success. Although the examples that follow demonstrate loading of red blood cells, the invention is not limited thereto; it is contemplated that other cells may be loaded as well, such as stem cells, bone marrow cells, platelets, granulocytes, lymphocytes including T and B cells, monocytes, neutrophils, eosinophils, plasma cells, macrophage, dendritic cells, or a cell of mesenchymal, ectodermal, or endodermal origin. Macrophages loaded with a texaphyrin-lipophilic molecule conjugate are expected to have utility in the treatment of atheroma since macrophages complex with cholesterol to form foam cells, a component of early atheroma Loaded vesicles will naturally biolocalize into the blood, liver, spleen, bone marrow or lymphoid organs. Due to the size of a vesicle, such as a red blood cell or a liposome, compared to the size of a texaphyrin-lipophilic molecule conjugate, it is expected that the vesicle will dominate in tenns of biolocalization, and any localizing effect of a site-directing lipophilic molecule or the inherent biolocalization of texaphyrins will be secondary. For example, a texaphyrin-estradiol conjugate loaded into a vesicle may have some specificity for an estradiol receptor if the estradiol is superficial to the vesicle. Similarly, a vesicle loaded with a texaphyrin-cholesterol conjugate may have localization to the liver in addition to the natural localization of the vesicle to the liver.

Human LDL is a physiologic serum protein metabolized by cells via uptake by high affinity receptors. In particular, neovascularization has been shown to have increased numbers of LDL receptors; and by increasing the partitioning of the texaphyrn into the lipoprotein phase of the blood, LDL is expected to more efficiently deliver texaphyrin to target tissue. A texaphyrin-LDL conjugate is selective for neovascularization since leakage of the conjugate is expected to occur only in neovasculature due to the large size of the conjugate. LDL can be isolated and purified according to the procedure of Hauel et al., (*J. Clin. Invest.*, 34:1345, 1995).

In the loading of red blood cells of the present invention, red blood cells are separated from plasma and washed in normal saline. They are then treated with hypertonic saline which leaves them crenated with their internal salt concentration being higher than normal. The crenated cell pellet is resuspended in hypotonic saline containing a texaphyrin-lipophilic molecule conjugate. Because of the concentration difference between the cell interior and the hypotonic solution, water and the conjugate are driven into the cells. The cells are then washed several times in normal saline. This procedure results in a red blood cell with extensive labeling with the texaphyrin-lipophilic molecule conjugate. Further methods for loading cells are known to those of skill in this art in light of the present disclosure and may be utilized in the preparation of complexes of the present invention, for example, inducing an osmotic difference by use of sucrose solutions, treating with calcium chloride or calcium phosphate, or the like.

White cells are obtained from blood by, for example, centrifugation through Ficoll Hypaque media. This separates the white blood cells from plasma components and red blood cells. Other techniques for obtaining specific types of cells are known to one of skill in the art in light of the present disclosure.

Liposomes may be prepared by any number of techniques that include freeze-thaw, sonication, chelate dialysis, homogenization, solvent infusion, microemulsification, spontaneous formation, solvent vaporization, reverse phase, French pressure cell technique, or controlled detergent dialysis, for example. Such preparation methods are known to one of skill in the art in light of the present disclosure. Preparation may be carried out in a solution, such as a phosphate buffer solution, containing a texaphyrin-lipophilic molecule conjugate so that the conjugate is incorporated into the liposome membrane. Alternatively, the conjugate may be added to already formed liposomes. Liposomes employed in the present invention may be of any one of a variety of sizes, preferably less than about 100 nm in outside diameter, more preferably less than about 50 nm.

Micelles may be prepared by suspension of a texaphyrin-lipophilic molecule and lipid compound(s) in an organic solvent, evaporation of the solvent, resuspension in an aqueous medium, sonication and then centrifugation. Alternatively, the texaphyrin-lipophilic molecule may be added to preformed micelles, which micelles are made by methods known by one of skill in the art in light of the present disclosure.

Techniques and lipids for preparing liposomes and micelles are discussed in U.S. Pat. No. 5,466,438, and references cited therein. The disclosures of each of the foregoing references are incorporated herein by reference.

A texaphyrin-lipophilic molecule conjugate as used herein is an aromatic pentadentate expanded porphyrin analog with appended functional groups, at least one of which is a lipophilic molecule. Pendant groups may enhance solubility or biolocalization or may provide coupling sites for site-directing molecules.

Examples of texaphyrin-lipophilic molecule conjugates are those having structure I or structure II:

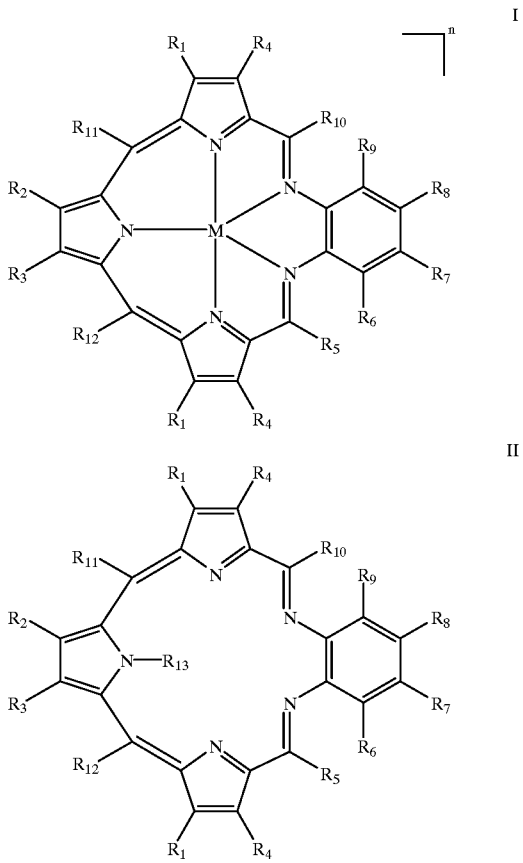

M is H, or a divalent or trivalent metal cation. A preferred divalent metal cation is Ca(II), Mn(II), Co(II), Ni(II), Zn(II), Cd(II), Hg(II), Fe(II), Sm(III), or UO$_2$(II). A preferred trivalent metal cation is Mn(III), Co(III), Ni(III), Fe(III), Ho(III), Ce(III), Y(III), In(III), Pr(III), Nd(III), Sm(III), Eu(III), Gd(III), Tb((III), Dy(III), Er(III), Tm(III), Yb(III), Lu(III), La(III), or U(III). Most preferred trivalent metal cations are Lu(III) and Gd(III).

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a lipophilic molecule, or a couple that is coupled to a lipophilic molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a couple that is coupled to a saccharide, or to a lipophilic molecule. The term "n" is an integer value less than or equal to 5.

$R_{13}$ is alkyl, alkenyl, oxyalkyl, or hydroxyalkyl having up to about 3 carbon atoms and having rotational flexibility around a first-bound carbon atom. Rotational flexibility allows the rest of the group to be positioned outside the plane of the texaphyrin. Thus, for example, a preferred alkenyl is $CH_2—CH=CH_2$. The pyrrole nitrogen substituent is most preferably a methyl group. A texaphyrin having a methyl group attached to a ring nitrogen is described in U.S. Pat. No. 5,457,183, incorporated by reference herein.

In this texaphyrin-lipophilic molecule conjugate, at least one of $R_1$–$R_{12}$ is a lipophilic molecule or a couple that is coupled to a lipophilic molecule. In a more preferred embodiment, at least one of $R_1$, $R_2$, $R_3$, $R_4$, $R_7$ and $R_9$ is a lipophilic molecule, and more preferably is estradiol or cholesterol, or a couple that is coupled to estradiol or cholesterol. In a presently preferred embodiment, the texaphyrin-lipophilic molecule conjugate is the conjugate depicted herein as $1_A$ or $1_B$.

Texaphyrins of the present conjugates may be metal-free or may be in a complex with a metal. Divalent and trivalent metal complexes of texaphyrins are by convention shown with a formal charge of $n^+$, where n=1 or 2, respectively. The value "n" will typically be an integer less than or equal to 5; however, one skilled in the art in light of the present disclosure would realize that the value of n would be altered due to any charges present on substituents $R_1$–$R_{12}$.

It is understood by those skilled in the art that texaphyrin-metal complexes have one or more additional ligands providing charge neutralization and/or coordinative saturation to the metal ion. Such ligands include chloride, nitrate, acetate, cholate, and hydroxide, among others.

Photosensitive texaphyrins are used for PDT. A photosensitive texaphyrin may be a free-base texaphyrin or may be metallated with a diamagnetic metal. The term "photosensitive," as used herein, means that upon photoirradiation by light associated with the absorption profile of texaphyrin, texaphyrin effects the generation of oxygen products that are cytotoxic. Cytotoxic oxygen products may be singlet oxygen, hydroxyl radicals, superoxide, hydroperoxyl radicals, or the like. A photosensitive texaphyrin may be a texaphyrin metal complex, and in this embodiment, the metal M is a diamagnetic metal cation and the diamagnetic metal cation preferably is Lu(III), La(III), In(III), Y(III), Zn(II) or Cd(II). A more preferred diamagnetic metal cation is Lu(III).

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonejne and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, and the term as used herein includes both unsubstituted aryls and aryls substituted with one or more nitro, carboxy, sulfonic acid, hydroxy, oxyalkyl or halide substituents. In this case, the substituent on the phenyl or naphthyl may be added in a synthetic step after the condensation step which forms the macrocycle.

Among the halide substituents, chloride, bromide, fluoride and-iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of $C_{1-10}$ alkyls being preferred, and diols of $C_{1-3}$ alkyls being more preferred; and polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. "Oxyalkyl" is meant to include polyethers with one or more functional groups. The number of repeating oxyalkyls within a substituent may be up to 200, preferably is from 1–20, and more preferably, is 1–10, and most preferably is 1–5. A preferred oxyalkyl is $O(CH_2CH_2O)_xCH_3$ where x=1–100, preferably 1–10, and more preferably, 1–5.

"Oxyhydroxyalkyl" means alkyl groups having ether or ester linkages, hydroxyl groups, substituted hydroxyl groups, carboxyl groups, substituted carboxyl groups or the like.

Representative examples of thioalkyls include thiols of ethane, thiols of straigth-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5)_2SO_4$).

Representative examples of phosphates include phosphate or polyphosphate groups. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of caboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R" is a functional group as described herein.

Representative examples of useful amines include a primary, secondary or tertiary amine of an alkyl as described hereinabove.

"Carboxyamidealkyl" means alkyl groups with secondary or tertiary amide linkages or the like. "Carboxyalkyl" means alkyl groups having hydroxyl groups, carboxyl or amide substituted ethers, ester linkages, tertiary amide linkages removed from the ether or the like.

The term "saccharide" includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugrs; oligosaccharides, as well as open chain forms of various sugars, and the like. Examples of amine-derivatized sugars are galactosamine, glucosamine, sialic acid and D-glucarine derivatives such as 1-amino-1-deoxysorbitol.

A couple may be described as a linker, i.e., the covalent product formed by reaction of a reactive group designed to attach covalently another molecule at a distance from the texaphyrin macrocycle. Exemplary linkers or couples are amides, amine, disulfide, thioether, ether, polyether, ester, or phosphate covalent bonds. PCT publication WO 94/29316 is incorporated by reference herein for providing syntheses of texaphyrin-conjugates having these types of linkages or couples.

In most preferred embodiments, conjugates and appended groups are covalently bonded to the texaphyrin via a carboncarbon, carbon-nitr6gen, carbon-sulfur, or a carbon-oxygen bond, more preferably a carbon-oxygen or a carbon-nitrogen bond.

In the practice of the present invention, preferred functionalizations for texaphyrin I or II are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$, and $R_{12}$ are independently hydrogen, phenyl, lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl. The phenyl may be substituted or unsubstituted.

In a presently preferred texaphyrin I or II, $R_1$ is $CH_2CH_3$ or $(CH_2)_2CH_2OH$; $R_2$ and $R_3$ are $CH_2CH_3$; $R_4$ is $CH_3$; $R_5$, $R_6$, and $R_9$–$R_{12}$ are H; $R_8$ is a lipophilic molecule or a couple that is coupled to a lipophilic molecule; and $R_7$ is H, OH, $OCH_3$ or $O(CH_2CH_2O)_xCH_3$ where x is 1–10 and preferably 1–5, more preferably 3. Preferably, $R_8$ is estradiol or cholesterol, or a couple that is coupled to estradiol or cholesterol.

A couple that is coupled to a lipophilic molecule may be further described as $O(CH_2CH_2O)_m$— where m is 1–10 and preferably 1–5, or as $O(CH_2)_nCO$— where n is 1–10 and preferably 1–3.

Presently preferred texaphyrin-lipophilic molecule conjugates, T2BET-estradiol conjugates, are provided as $1_A$ and $1_B$.

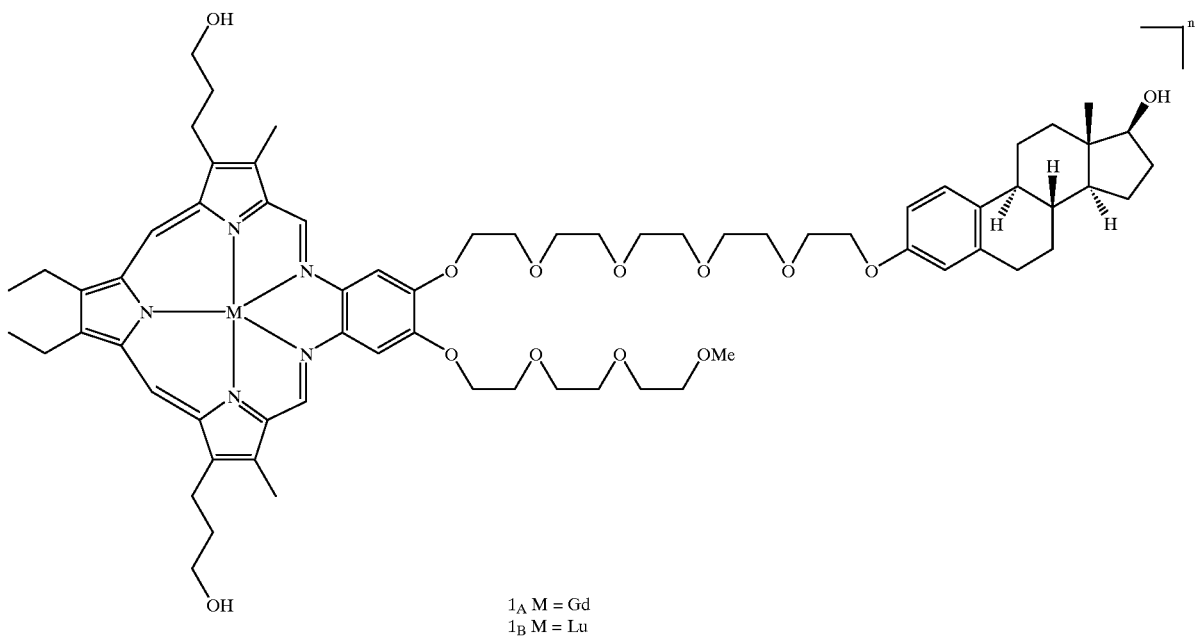

$1_A$ M = Gd
$1_B$ M = Lu

"T2" refers to two hydroxyl groups on the tripyrrane portion of texaphyrin, "BET" refers to the ethoxy R groups on the benzene portion of the molecule, and estradiol is the lipophilic molecule of this conjugate. The synthesis of this conjugate is provided in Example 1.

In other presently preferred texaphyrin compounds I or II, $R_1$–$R_{12}$ are as in Tables A and B for texaphyrins A1–A108, and M is as defined hereinabove. While the cited texaphyrins are presently prefenrrd for use in the present invention, the invention is not limited thereto.

TABLE A

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | H | H |
| A2 | " | " | " | " | " | " |
| A3 | " | " | " | " | " | " |
| A4 | " | " | " | " | " | " |
| A5 | " | " | " | " | " | " |
| A6 | " | " | " | " | " | " |
| A7 | " | " | " | " | " | " |
| A8 | " | " | " | " | " | " |
| A9 | " | " | " | " | " | " |
| A10 | " | " | " | " | " | " |
| A11 | " | " | " | " | " | " |
| A12 | " | COOH | COOH | " | " | " |
| A13 | $CH_2(CH_2)_2OH$ | $COOCH_2CH_3$ | $COOCH_2CH_3$ | $CH_3$ | H | H |
| A14 | $CH_2CH_2CON(CH_2CH_2OH)_2$ | $CH_2CH_3$ | $CH_2CH_3$ | " | " | " |
| A15 | $CH_2CH_2ON(CH_3)CH_2$—$(CHOH)_4CH_2OH$ | " | " | " | " | " |
| A16 | $CH_2CH_3$ | " | " | " | " | " |
| A17 | $CH_2(CH_2)_2OH$ | " | " | " | " | " |
| A18 | " | " | " | " | " | " |
| A19 | " | " | " | " | " | " |
| A20 | $CH_2CH_3$ | $CH_3$ | $CH_2CH_2COOH$ | " | " | " |
| A21 | " | " | $CH_2CH_2CO$-lipophilic molecule | " | " | " |
| A22 | $CH_2(CH_2)_2OH$ | $CH_2CH_3$ | $CH_2CH_3$ | " | " | " |
| A23 | " | " | " | " | " | " |
| A24 | " | " | " | " | " | " |
| A25 | " | " | " | " | " | " |
| A26 | " | " | " | " | " | " |
| A27 | " | COOH | COOH | " | " | " |
| A28 | " | $COOCH_2CH_3$ | $COOCH_2CH_3$ | " | " | " |
| A29 | $CH_2CH_2CO$-lipophilic molecule | $CH_2CH_3$ | $CH_2CH_3$ | $CH_3$ | H | H |
| A30 | $CH_2CH_2O$-lipophilic molecule | " | " | " | " | " |
| A31 | $CH_2(CH_2)_2OH$ | " | $CH_2CH_2CO$-lipophilic molecule | " | " | " |
| A32 | " | " | $CH_2CH_2CO$-lipophilic molecule | " | " | " |
| A33 | $CH_2CH_3$ | $CH_3$ | $CH_2CH_2COOH$ | " | " | " |
| A34 | " | " | $CH_2CH_2CO$-lipophilic molecule | " | " | " |
| A35 | $CH_2CH_3$ | $CH_2CH_3$ | $CH_2CH_3$ | " | " | " |
| A36 | " | " | " | " | " | " |
| A37 | " | " | " | " | " | " |
| A38 | " | " | " | " | " | " |
| A39 | $CH_2(CH_2)_2OH$ | $CH_2CH_3$ | $CH_2CH_3$ | $CH_3$ | H | COOH |
| A40 | " | " | " | " | " | COOH |
| A41 | " | " | " | " | " | CONHCH—$(CH_2OH)_2$ |
| A42 | " | " | " | " | " | CONHCH—$(CH_2OH)_2$ |
| A43 | " | " | " | " | " | H |
| A44 | " | " | " | " | " | $OCH_3$ |
| A45 | " | " | " | " | " | " |
| A46 | " | " | " | " | " | " |
| A47 | " | " | " | " | " | " |
| A48 | " | " | " | " | " | " |
| A49 | " | " | " | " | " | " |
| A50 | " | " | " | " | " | $CH_3$ |
| A51 | " | " | " | " | " | " |
| A52 | " | " | " | " | " | " |
| A53 | " | " | " | " | " | " |
| A54 | " | " | " | " | $CH_3$ | H |
| A55 | " | " | " | " | " | " |
| A56 | " | " | " | " | " | " |
| A57 | $CH_2(CH_2)_2OH$ | $CH_2CH_3$ | $CH_2CH_3$ | $CH_3$ | $CH_3$ | H |
| A58 | " | " | " | " | " | " |
| A59 | " | " | " | " | " | " |
| A60 | " | " | " | " | " | " |
| A61 | " | " | " | " | " | " |
| A62 | " | " | " | " | " | " |
| A63 | " | " | " | " | " | OH |
| A64 | " | " | " | " | " | F |
| A65 | " | " | " | " | $CH_2(CH_2)_6OH$ | H |
| A66 | " | " | " | " | H | Br |

TABLE A-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_1$ | $R_2$ | $R_3$ | $R_4$ | $R_5$ | $R_6$ |
|---|---|---|---|---|---|---|
| A67 | " | " | " | " | " | $NO_2$ |
| A68 | " | " | " | " | " | COOH |
| A69 | " | " | " | " | " | $CH_3$ |
| A70 | " | " | " | " | $C_6H_5$ | H |
| A71 | " | COOH | COOH | " | $CH_2CH_3$ | " |
| A72 | " | $COOCH_2CH_3$ | $COOCH_2CH_3$ | " | $CH_3$ | " |
| A73 | $CH_2CH_2CON(CH_2CH_2OH)_2$ | $CH_2CH_3$ | $CH_2CH_3$ | " | " | " |
| A74 | $CH_2CH_2ON(CH_3)CH_2$(CHOH)$_4CH_2OH$ | " | " | " | " | " |
| A75 | $CH_2CH_3$ | $CH_2CH_3$ | " | " | $CH_2(CH_2)_6OH$ | " |
| A76 | $CH_2(CH_2)_2OH$ | $CH_2CH_3$ | $CH_2CH_3$ | $CH_3$ | $CH_3$ or $CH_2CH_3$ | H |
| A77 | " | " | " | " | " | " |
| A78 | " | " | " | " | " | " |
| A79 | " | " | " | " | " | " |
| A80 | " | " | " | " | " | " |
| A81 | " | " | " | " | " | " |
| A82 | " | " | " | " | " | " |
| A83 | " | " | " | " | " | " |
| A84 | " | " | " | " | " | " |
| A85 | " | " | " | " | H | " |
| A86 | " | " | " | " | " | " |
| A87 | " | " | " | " | $CH_3$ or $CH_2CH_3$ | " |
| A88 | " | " | " | " | " | " |
| A89 | " | " | " | " | " | " |
| A90 | " | " | " | " | " | " |
| A91 | " | " | " | " | " | " |
| A92 | " | " | " | " | " | " |
| A93 | " | COOH | COOH | " | " | " |
| A94 | " | $COOCH_2CH_3$ | $COOCH_2CH_3$ | " | " | " |
| A95 | $CH_2(CH_2)_2OH$ | $CH_2CH_3$ | $CH_2CH_2CO$-lipiphilic molecule | " | " | " |
| A96 | $CH_2CH_3$ | $CH_3$ | $CH_2CH_2COOH$ | " | " | " |
| A97 | " | " | $CH_2CH_2CO$-lipiphilic molecule | " | " | " |
| A98 | $CH_2(CH_2)_2OH$ | $CH_2CH_3$ | $CH_2CH_3$ | " | " | " |
| A99 | $CH_2CH_3$ | " | " | " | " | " |
| A100 | " | " | " | " | " | " |
| A101 | " | " | " | " | " | " |
| A102 | " | " | " | " | " | " |
| A103 | " | " | " | " | " | " |
| A104 | " | " | " | " | " | " |
| A105 | $CH_2(CH_2)_2OH$ | " | " | " | " | " |
| A016 | " | " | " | " | " | " |
| A107 | " | " | " | " | " | " |
| A108 | " | " | " | " | " | " |

TABLE B

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A1 | $O(CH_2)_3OH$ | $O(CH_2)_3OH$ | H | H | H | H |
| A2 | $O(CH_2CH_2O)_3CH_3$ | $O(CH_2CH_2O)_3CH_3$ | " | " | " | " |
| A3 | $O(CH_2)_nCON$-linker-lipophilic molecule, n = 1–10 | " | " | " | " | " |
| A4 | $O(CH_2)_nCON$-linker-lipophilic molecule, n = 1–10 | H | " | " | " | " |
| A5 | $OCH_2CO$-lipophilic molecule | " | " | " | " | " |
| A6 | $O(CH_2CH_2O)_3CH_3$ | " | " | " | " | " |
| A7 | $OCH_2CON$-linker-lipophilic molecule | $O(CH_2CH_2O)_3CH_3$ | " | " | " | " |
| A8 | $OCH_2CO$-lipophilic molecule | " | " | " | " | " |
| A9 | $O(CH_2CH_2O)_{100}CH_3$ | " | " | " | " | " |
| A10 | $OCH_2CON(CH_2CH_2OH)_2$ | H | " | " | " | " |
| A11 | $CH_2CON(CH_3)CH_2$-(CHOH)$_4CH_2OH$ | " | " | " | " | " |
| A12 | $CH_2CON(CH_3)CH_2$-(CHOH)$_4CH_2OH$ | " | " | " | " | " |

TABLE B-continued

Representative Substituents for Texaphyrin Macrocycles A1–A108 of the Present Invention.
Substituents for R$_1$–R$_6$ are provided in TABLE A and for R$_7$–R$_{12}$ in TABLE B.

| TXP | R$_7$ | R$_8$ | R$_9$ | R$_{10}$ | R$_{11}$ | R$_{12}$ |
|---|---|---|---|---|---|---|
| A13 | CH$_2$CON(CH$_3$)CH$_2$-(CHOH)$_4$CH$_2$OH | H | H | H | H | H |
| A14 | CH$_2$CON(CH$_3$)CH$_2$-(CHOH)$_4$CH$_2$OH | " | " | " | " | " |
| A15 | OCH$_3$ | OCH$_3$ | " | " | " | " |
| A16 | OCH$_2$CO$_2$-lipophilic molecule | H | " | " | " | " |
| A17 | O(CH$_2$)$_n$COOH, n = 1–10 | " | " | " | " | " |
| A18 | (CH$_2$)$_n$-CON-linker-lipophilic molecule, n = 1–10 | " | " | " | " | " |
| A19 | YCOCH$_2$-linker-lipophilic molecule, Y = NH,O | " | " | " | " | " |
| A20 | O(CH$_2$)$_2$CH$_2$OH | O(CH$_2$)$_2$CH$_2$OH | " | " | " | " |
| A21 | " | " | " | " | " | " |
| A22 | OCH$_2$COOH | O(CH$_2$CH$_2$O)$_3$CH$_3$ | " | " | " | " |
| A23 | O(CH$_2$)$_n$CO-lipophilic molecule, n = 1–10 | H | " | " | " | " |
| A24 | O(CH$_2$CH$_2$O)$_3$CH$_3$ | O(CH$_2$CH$_2$O)$_n$-lipophilic molecule, n = 1–10, in particular, n = 3 or 5 | " | " | " | " |
| A25 | OCH$_3$ | OCH$_2$CO-lipophilic molecule | " | " | " | " |
| A26 | " | CH$_2$CO-lipophilic molecule | " | " | " | " |
| A27 | " | " | " | " | " | " |
| A28 | OCH$_3$ | CH$_2$CO-lipophilic molecule | H | H | H | H |
| A29 | " | OCH$_3$ | " | " | " | " |
| A30 | " | " | " | " | " | " |
| A31 | H | O(CH$_2$)$_n$COOH, n = 1–10 | " | " | " | " |
| A32 | " | (CH$_2$)$_n$-CON-linker-lipophilic molecule, n = 1–10 | " | " | " | " |
| A33 | OCH$_3$ | O(CH$_2$CH$_2$O)$_3$—CH$_3$ | " | " | " | " |
| A34 | " | " | " | " | " | " |
| A35 | H | O(CH$_2$)$_n$CO-lipophilic molecule, n = 1–10 | " | " | " | " |
| A36 | OCH$_3$ | O(CH$_2$)$_n$CO-lipophilic molecule, n = 1–10 | " | " | " | " |
| A37 | O(CH$_2$CH$_2$O)$_3$CH$_3$ | O(CH$_2$)$_n$CO-lipophilic molecule, n = 1–10 | " | " | " | " |
| A38 | " | O(CH$_2$CH$_2$O)$_n$-lipophilic molecule, n = 1–10 | " | " | " | " |
| A39 | O(CH$_2$)$_3$OH | O(CH$_2$)$_3$OH | O(CH$_2$)$_3$OH | H | H | H |
| A40 | O(CH$_2$CH$_2$O)$_3$CH$_3$ | O(CH$_2$CH$_2$O($_3$CH$_3$ | COOH | " | " | " |
| A41 | O(CH$_2$CH$_2$O)$_3$CH$_3$ | O(CH$_2$CH$_2$O)$_3$CH$_3$ | (CH$_2$)$_3$OH | " | " | " |
| A42 | " | " | O(CH$_2$CH$_2$O)$_3$CH$_3$ | " | " | " |
| A43 | " | O(CH$_2$)$_3$COOH | " | " | " | " |
| A44 | H | OCH$_2$COOH | OCH$_3$ | " | " | " |
| A45 | " | OCH$_2$COOH | " | " | " | " |
| A46 | " | O(CH$_2$CH$_2$O)$_3$CH$_3$ | " | " | " | " |
| A47 | O(CH$_2$CH$_2$O)$_3$CH$_3$ | " | " | " | " | " |
| A48 | " | OCH$_2$CO-lipophilic molecule | " | " | " | " |
| A49 | " | OCH$_2$COOH | " | " | " | " |
| A50 | " | O(CH$_2$CH$_2$O)$_3$CH$_3$ | O(CH$_2$CH$_2$O)CH$_3$ | " | " | " |
| A51 | " | OCH$_2$COOH | " | " | " | " |
| A52 | O(CH$_2$CH$_2$O)$_3$CH$_3$ | O(CH$_2$CH$_2$O)$_{100}$CH$_3$ | OCH$_3$ | " | " | " |
| A53 | H | OCH$_2$CO-lipophilic molecule | " | " | " | " |
| A54 | O(CH$_2$)$_3$OH | O(CH$_2$)$_3$OH | H | CH$_3$ | " | " |
| A55 | H | O(CH$_2$CH$_2$O)$_3$CH$_3$ | " | " | " | " |
| A56 | O(CH$_2$CH$_2$O)$_3$CH$_3$ | " | " | " | " | " |
| A57 | H | OCH$_2$CO-lipophilic molecule | H | CH$_3$ | " | " |
| A58 | " | OCH$_2$CO-lipophilic molecule | " | " | " | " |
| A59 | " | OCH$_2$CON(CH$_2$CH$_2$OH)$_2$ | " | " | " | " |
| A60 | O(CH$_2$CH$_2$O)$_3$CH$_3$ | O(CH$_2$CH$_2$O)$_{100}$CH$_3$ | " | " | " | " |
| A61 | " | OCH$_2$CO-lipophilic molecule | " | " | " | " |
| A62 | H | CH$_2$CON(CH$_3$)CH$_2$(CHOH)$_4$CH$_2$OH | " | " | " | " |
| A63 | O(CH$_2$CH$_2$O)$_3$CH$_3$ | O(CH$_2$CH$_2$O)$_3$CH$_3$ | OH | " | " | " |
| A64 | " | " | F | " | " | " |
| A65 | " | " | H | CH$_2$(CH$_2$)$_6$OH | " | " |
| A66 | " | " | Br | H | " | " |

TABLE B-continued

Representative Substituents for Texaphyrin Macrocycles A1–A108 of the Present Invention.
Substituents for $R_1$–$R_6$ are provided in TABLE A and for $R_7$–$R_{12}$ in TABLE B.

| TXP | $R_7$ | $R_8$ | $R_9$ | $R_{10}$ | $R_{11}$ | $R_{12}$ |
|---|---|---|---|---|---|---|
| A67 | " | " | $NO_2$ | " | " | " |
| A68 | " | " | COOH | " | " | " |
| A69 | " | " | $CH_3$ | " | " | " |
| A70 | " | " | H | $C_6H_5$ | " | " |
| A71 | " | " | " | $CH_2CH_3$ | " | " |
| A72 | " | " | " | $CH_3$ | " | " |
| A73 | " | " | " | " | " | " |
| A74 | $OCH_3$ | $OCH_3$ | " | " | " | " |
| A75 | H | $OCH_2CO$-lipophilic molecule | " | $CH_2(CH_2)_6OH$ | " | " |
| A76 | $O(CH_2)_3OH$ | $O(CH_2)_3OH$ | H | $CH_3$ or $CH_2CH_3$ | $CH_3$ or $CH_2CH_3$ | $CH_3$ or $CH_2CH_3$ |
| A77 | $O(CH_2CH_2O)_3CH_3$ | $O(CH_2CH_2O)_3CH_3$ | " | $CH_3$ or $CH_2CH_3$ | $CH_3$ or $CH_2CH_3$ | $CH_3$ or $CH_2CH_3$ |
| A78 | $O(CH_2)_3OH$ | $O(CH_2CH_2O)_3CH_3$ | " | $CH_3$ or $CH_2CH_3$ | $CH_3$ or $CH_2CH_3$ | $CH_3$ or $CH_2CH_3$ |
| A79 | H | $O(CH_2)_nCO$-lipophilic molecule, n = 1,2,3 | " | $CH_3$ or $CH_2CH_3$ | $CH_3$ or $CH_2CH_3$ | $CH_3$ or $CH_2CH_3$ |
| A80 | H | $O(CH_2)_nCO$-lipophilic molecule, n = 1,2,3 | " | $CH_3$ or $CH_2CH_3$ | $CH_3$ or $CH_2CH_3$ | $CH_3$ or $CH_2CH_3$ |
| A81 | H | $O(CH_2)_3OH$ | " | $CH_3$ or $CH_2CH_3$ | $CH_3$ or $CH_2CH_3$ | $CH_3$ or $CH_2CH_3$ |
| A82 | $O(CH_2)_3OH$ | $O(CH_2)_nCO$-lipophilic molecule, n = 1,2,3, | " | $CH_3$ or $CH_2CH_3$ | $CH_3$ or $CH_2CH_3$ | $CH_3$ or $CH_2CH_3$ |
| A83 | $O(CH_2CH_2O)_3CH_3$ | $O(CH_2)_nCO$-lipophilic molecule, n = 1–10 | " | $CH_3$ or $CH_2CH_3$ | $CH_3$ or $CH_2CH_3$ | $CH_3$ or $CH_2CH_3$ |
| A84 | " | $O(CH_2)_nCO$-lipophilic molecule, n = 1,2,3 | " | $CH_3$ or $CH_2CH_3$ | $CH_3$ or $CH_2CH_3$ | $CH_3$ or $CH_2CH_3$ |
| A85 | " | $O(CH_2CH_2O)_3CH_3$ | " | $CH_3$ or $CH_2CH_3$ | $CH_3$ or $CH_2CH_3$ | $CH_3$ or $CH_2CH_3$ |
| A86 | " | " | " | $CH_3$ or $CH_2CH_3$ | $CH_2(CH_2)_2OH$ | $CH_2(CH_2)_2OH$ |
| A87 | " | " | " | $CH_3$ or $CH_2CH_3$ | " | " |
| A88 | " | $O(CH_2CH_2O)_3CH_3$ | " | $CH_3$ or $CH_2CH_3$ | " | " |
| A89 | $O(CH_2CH_2O)_3CH_2$—$CH_2$-lipophilic molecule | $O(CH_2CH_2O)_{120}CH_3$ | H | H | H | H |
| A90 | H | lipophilic molecule | " | " | " | " |
| A91 | $OCH_2CO$-lipophilic molecule | $OCH_2CO$-lipophilic molecule | " | " | " | " |
| A92 | $CH_2CO$-lipophilic molecule | $CH_2CO$-lipophilic molecule | " | " | " | " |
| A93 | " | " | " | " | " | " |
| A94 | " | " | " | " | " | " |
| A95 | H | $YCOCH_2$-linker-lipophilic molecule Y = NH,O | " | " | " | " |
| A96 | $O(CH_2CH_2O)_3CH_3$ | $O(CH_2CH_2O)_5$-lipophilic molecule | " | " | " | " |
| A97 | " | $O(CH_2CH_2O)_5$-lipophilic molecule | " | " | " | " |
| A98 | H | $O(CH_2)_3CO$-lipophilic molecule | " | " | " | " |
| A99 | " | $O(CH_2)_3CO$-lipophilic molecule | " | " | " | " |
| A100 | $OCH_3$ | $O(CH_2)_3CO$-lipophilic molecule | " | " | " | " |
| A101 | $O(CH_2CH_2O)_3CH_3$ | $O(CH_2)_3CO$-lipophilic molecule | " | " | " | " |
| A102 | " | $O(CH_2CH_2O)_5$-estradiol | " | " | " | " |
| A103 | " | $O(CH_2CH_2O)_n$-estradiol, n = 1–10 | " | " | " | " |
| A104 | " | $O(CH_2CH_2O)_n$-cholesterol, n = 1–10 | " | " | " | " |
| A105 | " | $O(CH_2CH_2O)_n$-cholesterol, n = 1–10 | " | " | " | " |
| A106 | $OCH_3$ | $O(CH_2CH_2O)_n$-estradiol, n = 1–10 | " | " | " | " |
| A107 | H | $O(CH_2CH_2O)_n$-estradiol, n = 1–10 | " | " | " | " |
| A108 | $O(CH_2CH_2O)_xCH_3$, x = 1–10 | $O(CH_2CH_2O)_n$-estradiol, n = 1–10 | " | " | " | " |

One skilled in the art of organic synthesis in light of the present disclosure and the disclosures in the patents, applications and publications incorporated by reference herein could extend and refine the referenced basic synthetic chemistry to produce texaphyrins having various substituents. For example, polyether-linked polyhydroxylated groups, saccharide substitutions in which the saccharide is appended via an acetal-like glycosidic linkage, an oligosaccharide or a polysaccharide may be similarly linked to a texaphyrin. A doubly carboxylated texaphyrin in which the carboxyl groups are linked to the texaphyrin core via aryl ethers or functionalized alkyl substituents could be converted to various esterified products wherein the ester linkages serve to append further hydroxyl-containing substituents. Polyhydroxylated texaphyrin derivatives may be synthesized via the use of secondary amide linkages. Saccharide moieties may be appended via amide bonds. Polyhydroxylated texaphyrin derivatives containing branched polyhydroxyl (polyol) subunits may be appended to the texaphyrin core via aryl ethers or ester linkages.

Treatment of carboxylated texaphyrins with thionyl chloride or p-nitrophenol acetate would generate activated acyl species suitable for attachment to monoclonal antibodies or other biomolecules of interest. Standard in situ coupling methods (e.g., 1,1'-carbonyldiimidazole) could be used to effect the conjugation.

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine. A lipophilic molecule may be added after the condensation step to form the texaphyrin macrocycle.

Lipophilic molecules having an amine functionality are modified post-synthetically with an activated carboxylic ester derivative of a texaphyrin. In the presence of a Lewis acid such as $FeBr_3$, a bromide-derivatized texaphyrin will react with an hydroxyl group of a lipophilic molecule to form an ether linkage between the texaphyrin linker and the lipophilic molecule. A couple that is coupled to a lipophilic molecule may be further described as $O(CH_2CH_2O)_m$— where m is 1–10 and preferably 1–5, or as $O(CH_2)_nCO$— where n is 1–10 and preferably 1–3.

Texaphyrin-lipophilic molecule conjugates may be made by methods as described herein and as known and described in the art, such as in U.S. patents, in pending applications, previously incorporated by reference herein. Texaphyrins have a number of properties that lend themselves for use in imaging and photodynamic treatment protocols, for example: texaphyrins have inherent biolocalization, localizing to tumors, atheroma, or the liver; they have absorption in the physiologically important range of 700–900 nm; they provide stable chelation for an otherwise toxic metallic cation; and are sufficiently nontoxic for in vivo use.

An aspect of the present invention is use of texaphyrin-lipophilic molecules or texaphyrin-lipophilic molecule-vesicle complexes in ocular diagnosis and therapy; especially diagnostic angiograms, and photodynamic therapy of conditions of the eye characterized by abnormal vasculature. "Abnormal vasculature", as used herein, means undesirable vasculature; neovasculature; irregular, occluded, weeping, or inflamed ocular vessels or ocular tissues; inflammatory ocular membranes; abnormal conditions having to do with channeling of fluids in the ocular area, especially blood vessels; and includes conditions such as macular degeneration, glaucoma, disc or retinal neovascularization in diabetic retinopathy, pannus which is abnormal superficial vascularization of the cornea or conjunctiva, pterygium which is thickening of the bulbar conjunctiva on the cornea, conditions having retinal or choroidal neovasculature, ocular histoplasmosis syndrome, myopia, ocular inflammatory diseases, central serous retinopathy, subretinal neovascular membrane, or neovasculature induced by neoplasm, such as melanoma or retinal blastoma, for example.

"Observing the vasculature", as used herein, means carrying out an imaging procedure and collecting information from an angiogram where fluorescent texaphyrins are used, from an x-ray, or from magnetic resonance image, for example, to interpret the condition of the eye. The condition of the eye may be normal, or may include vascular leakage or occlusions, for example. As used herein, "eye" or "ocular" includes the eye, underlying and adjacent tissue, and related tissues near and around the eye that have an influence on the functioning of the eye.

The parameters used for effective angiography and effective treatment in PDT methods of the invention are interrelated. Therefore, the dose is adjusted with respect to other parameters, for example, fluence, irradiance, duration of the light used in photodynamic therapy, and the time interval between administration of the dose and the therapeutic irradiation. Such parameters should be adjusted to produce significant damage to abnormal vascular tissue without significant damage to the surrounding tissue or, on the other hand, to enable the observation of blood vessels in the eye without significant damage to the surrounding tissue. Typically, the dose of texaphyrin of the texaphyrin-lipophilic molecule conjugate or texaphyrin-lipophilic molecule-vesicle complex used is within the range of from about 0.1 to about 50 µmol/kg/treatment, and preferably from about 0.10–20 µmol/kg/treatment. Further, as the texaphyrin dose is reduced, the fluence required to treat neovascular tissue may change.

After the photosensitizing texaphyrin-lipophilic molecule conjugate or texaphyrin-lipophilic molecule-vesicle complex has been administered, the tissue being treated in the eye is irradiated at the wavelength of maximum absorbance of the texaphyrin, usually either about 400–500 nm or about 700–800 nm. The light source may be a laser, a light-emitting diode, or filtered light from, for example, a xenon lamp; the light may have a wavelength range of about 400–900 nm, preferably about 400–500 nm or 700–800 nm, more preferably about 730–770 nm; and the light may be administered topically, endoscopically, or interstitially (via, e.g., a fiber optic probe). Preferably, the light is administered using a slit-lamp delivery system. A wavelength in this range is especially preferred since blood and retinal pigment epithelium are relatively transparent at longer wavelengths and, therefore, treatment results in less tissue damage and better light penetration. The fluence and irradiance during the irradiating treatment can vary depending on type of tissue, depth of target tissue, and the amount of overlying fluid or blood.

The optimum length of time following texaphyrin-lipophilic molecule conjugate or texaphyrin-lipophilic molecule-vesicle complex administration until light treatment can vary depending on the mode of administration, the form of administration, and the type of target tissue. For example, a time interval of minutes to about 5 h should be appropriate for vascular tissue. The time of light irradiation after administration may be important as one way of maximizing the selectivity of the treatment, thus minimizing damage to structures other than the target tissues. For a human, it is believed that the texaphyrin-lipophilic molecule conjugate or texaphyrin-lipophilic molecule-vesicle complex begins to reach the retinal and choroidal vasculature within seconds following administration, and persists for a period of minutes to hours, depending on the dose given. Treatment within the first five minutes following administration should generally be activated with focused light. At later time points, both focused or general illumination may be used.

In addition, texaphyrin-lipophilic molecule conjugate or texaphyrin-lipophilic molecule-vesicle complex can be used to observe the condition of blood vessels as a single agent, or in concert with other dyes such as fluorescein or indocyanine green to follow the progress of destruction of abnormal vascular tissue. In such angiographic systems, a sufficient amount of texaphyrin-lipophilic molecule conjugate or texaphyrin-lipophilic molecule-vesicle complex is administered to produce an observable fluorescent emission when excited by light, preferably light having a wavelength in the range of about 430–480 nm. Images are recorded by illuminating the eye with light in the excitation wavelength range and detecting the amount of fluorescent light emitted at the emission wavelength of about 730–760 nm. A preferred device, which both emits and receives light in the 430–760 nm range, is the TOPCON™ 50VT camera in the Ophthalmic Imaging System (Ophthalmic Imaging System Inc., 221 Lathrop Way, Suite 1, Sacramento Calif.).

A camera is used to collect the emitted fluorescent light, digitize the data, and store it for later depiction on a video screen, as a hard paper copy, or in connection with some other imaging system. While a film recording device may be used when additional dyes such as fluorescein are being used in combination with the texaphyrin-lipophilic molecule conjugate or texaphyrin-lipophilic molecule-vesicle complex, a CCD camera (charge-coupled device) is preferable as being able to capture emissions at higher wavelengths. As a result, one can obtain more sophisticated information regarding the pattern and extent of vascular structures in different ocular tissue layers, giving the ability to detect the "leakiness" that is characteristic of new or inflamed blood vessels. Further, it is preferable to use a camera that is capable of providing the excitation light, appropriately filtered to deliver only light of the desired excitation wavelength range, and then to capture the emitted, fluorescent light with a receiving device, appropriately filtered to receive only light in the desired emission wavelength range.

For the above-described uses, texaphyrin-lipophilic molecule-cell or -liposome complexes are provided as pharmaceutical preparations. A pharmaceutical preparation of such a complex may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a complex of the present invention and the pharmaceutically acceptable carriers are then easily administered in a variety of dosage forms such as injectable solutions.

For parenteral administration, suspensions of the liposomal complex in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Intravenous administration of loaded red or white blood cell complexes of the present invention is contemplated as the most preferred method of administration.

Sterile technique is used for removal of cells from a patient, loading with a sterile texaphyrin-lipophilic molecule conjugate and replacement of loaded cells into the same patient. A pharmaceutically acceptable carrier may be used, which carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration.

Sterile conjugate solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

For fluorescent detection methods of the present invention, a sufficient amount of texaphyrin is administered to produce an observable fluorescent emission when excited by light, preferably light having a wavelength in the range of about 430–480 nm. Images are recorded by illuminating with light in the excitation wavelength range and detecting the amount of fluorescent light emitted at the emission wavelength of preferably about 730–760 nm. Such dose can be determined without undue experimentation by methods known in the art or as described herein.

The complexes to be used in the photodynamic methods of the present invention are administered in a pharmaceutically effective amount. By "pharmaceutically effective" is meant that dose which will, upon exposure to light, cause disruption of the loaded vesticle. The specific dose will vary depending on the particular complex chosen, the dosing regimen to be followed, photoirradiation exposure, and timing of administration. Such dose can be determined without undue experimentation by methods known in the art or as described herein.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of a Texaphyrin-Lipophilic Molecule Conjugate

The present example provides the synthesis of a texaphyrin-lipophilic molecule conjugate where the lipophilic molecule is estradiol. The synthetic route is provided by Schematic A.

Penta(ethyleneglycol) diiodide (2). Penta(ethyleneglycol) ditosylate 1 (25 g, Aldrich Chemical, Milwaukee, Wis.), sodium iodide (17.15 g, 2.5 eq.), and acetone (ca. 500 mL) were combined and heated at reflux for 4 hours; Upon cooling, solids were removed by filtration and washed with acetone. Acetone was removed from the combined filtrate and washed by rotary evaporation. The resulting solid was dissolved in $CHCl_3$ (250 ml), and washed with water (250 mL), a 5% aqueous solution of $Na_2S_2O_3$ (2×250 mL) and water (250 mL). Solvent was removed by rotary evaporation and the resulting solid dried in vacuo to give diiodide 2 (19.164 g, 91.3%).

3-(2-(Ethoxy-2-(ethoxy-2-(ethoxy-(2-iodoethoxy)))) ethoxy)17β-hydroxy-3-oxy-1,3,5(10)-estratriene (4). The diiodide 2 (12.50 g), β-estradiol 3 (2.500 g, Aldrich Chemical, Milwaukee, Wis.), potassium carbonate (1.500 g) and anhydrous acetonitrile (250 mL) were combined in a flask. The reaction mixture was heated at reflux for 9 hours, whereupon it was allowed to cool in ambient temperature, and solvent removed by rotary evaporation. The residue was dissolved in $CHCl_3$ (125 mL), washed with water, and solvent removed by rotary evaporation. The crude product was purified by silica gel chromatography using 0.5 to 1.0% MeOH in $CHCl_3$ as eluent. Fractions containing only product were combined, solvent was removed by rotary evaporation, and the residue dried in vacua to give iodide 4 (2.010 g, 36.4%).

Dinitrobenzene sodium salt (5), method one. The dinitrobenzene sodium salt 5 was prepared by reacting 4,5-dinitrocatechol (5 g, 0.025 mol) and triethylene glycol monomethyl ether monotosylate (11.9 g, 0.037 mol, 1.5 eq.) with $K_2CO_3$ (5.18 g, 0.037 mol, 1.5 eq.) in methanol, with heating to reflux under nitrogen atmosphere overnight. The reaction was allowed to cool to RT, and the solvent was removed under reduced pressure. The residue was then resuspended into 250 mL of 1M NaOH, after which chloroform was added. The lower chloroform layer plus precipitate were drained off and the orange solid precipitate was collected by filtration and vacuum dried under high vacuum overnight to give the light orange solid product 5, in 81% yield.

Dinitrobenzene Sodium Salt (5), method two. An alternate method of synthesis of the dinitrobenzene sodium salt is as follows. In a dry 250 mL round bottom flash, 4,5-dinitrocatechol (10 g, 0.050 mol) and $K_2CO_3$ (10.37 g, 0.075 mol) were combined in absolute methanol (120 mL) under nitrogen atmosphere. To the orange mixture, triethylene glycol monomethyl ether tosylate (23.85 g, 0.075 mol) was added and the resulting suspension was heated to reflux. The reaction was deemed complete by TLC analysis by the disappearance of the starting catechol and appearance of the bright yellow monoalkylated intermediate. Therefore, after 16 h the red suspension was cooled to 0° C. The resulting suspension was filtered, washed thoroughly with cold isopropyl alcohol (50 mL) and hexanes (50 mL). The monoalkylated potassium salt was then suspended in 10% aqueous NaOH (100 mL), vigorously stirred for 15–20 min at room temperature, filtered, and then rinsed thoroughly with cold isopropyl alcohol (70 mL) and hexanes (50 mnL). (This step aids the removal of excess $K_2CO_3$ and potassium tosylate). The bright orange salt was dried in vacuo and afforded 15 g (~81%). $^1H$ NMR ($d_6$ acetone): selected peaks, δ3.40 (OMe), 6.30 (ArH), 7.42 (ArH); EI MS (M+Na$^+$) 369; EI HRMS (M+Na$^+$) 369.0910 (calcd. for $C_{13}H_{18}N_2O_9Na$ 369.0910).

Schematic A

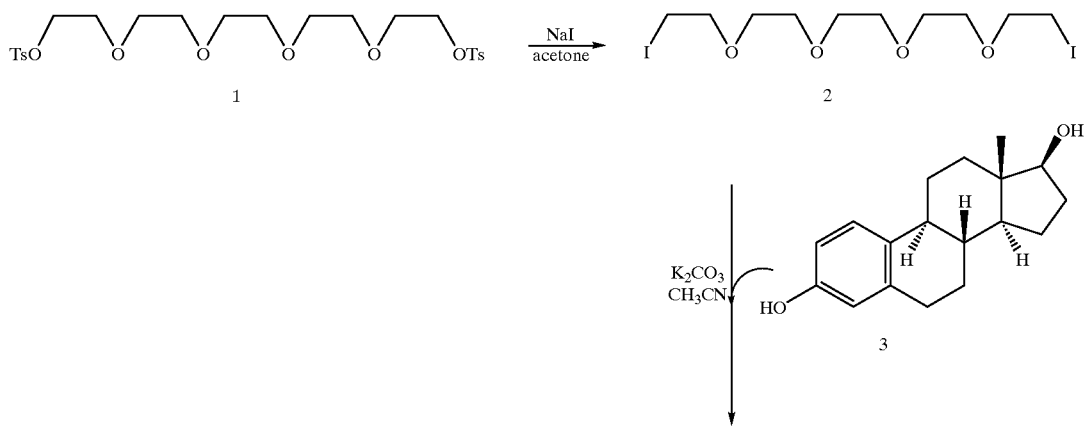

-continued
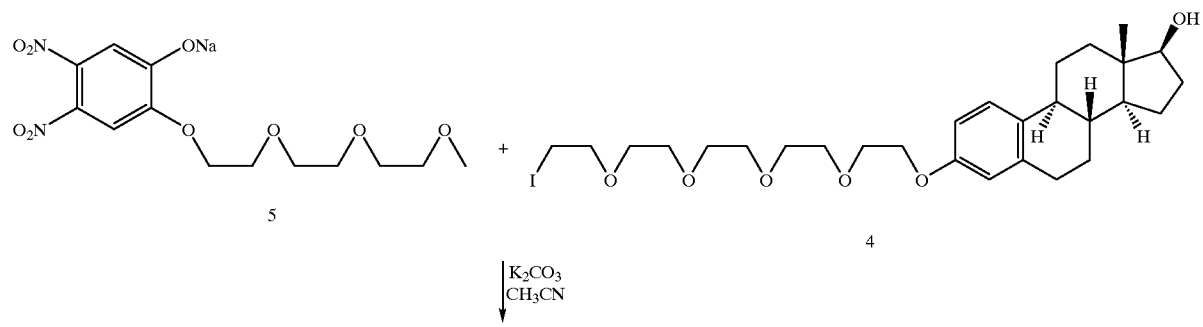
5
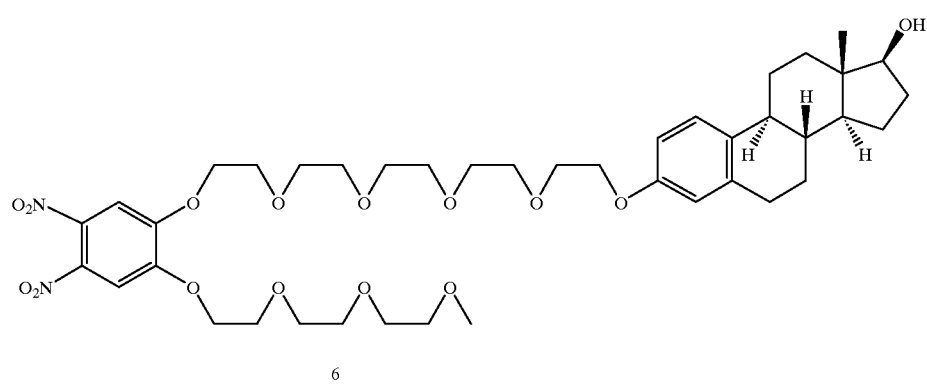
6
↓ K₂CO₃
  CH₃CN
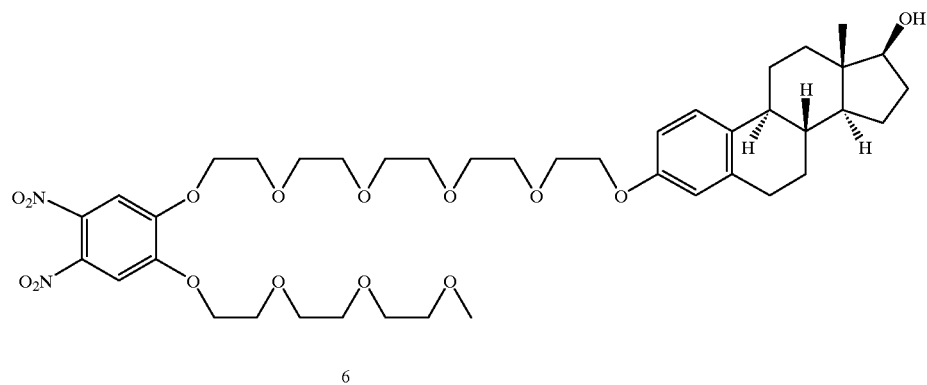
6
↓ 10% Pd/C
  H₂ gas
  2 eq. conc. HCl
  methanol
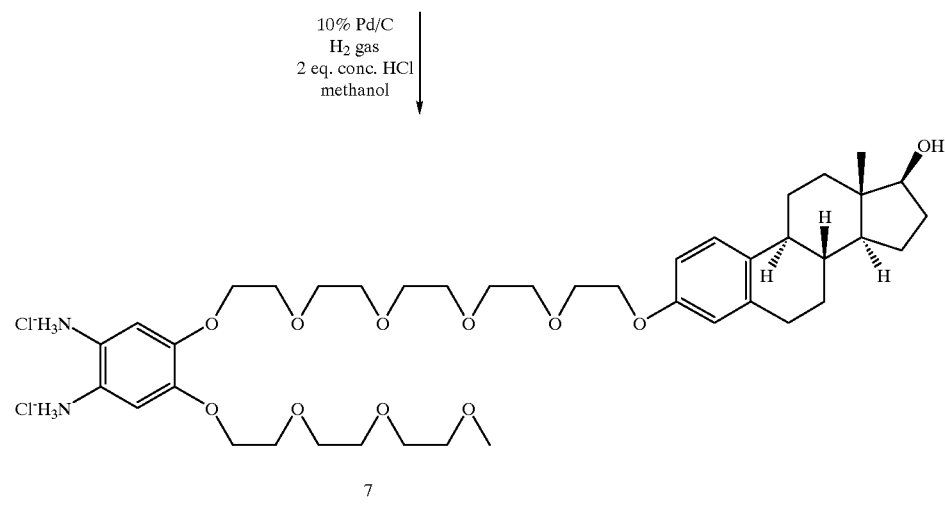
7

-continued
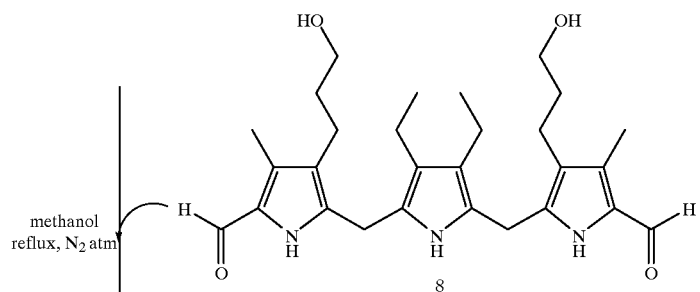
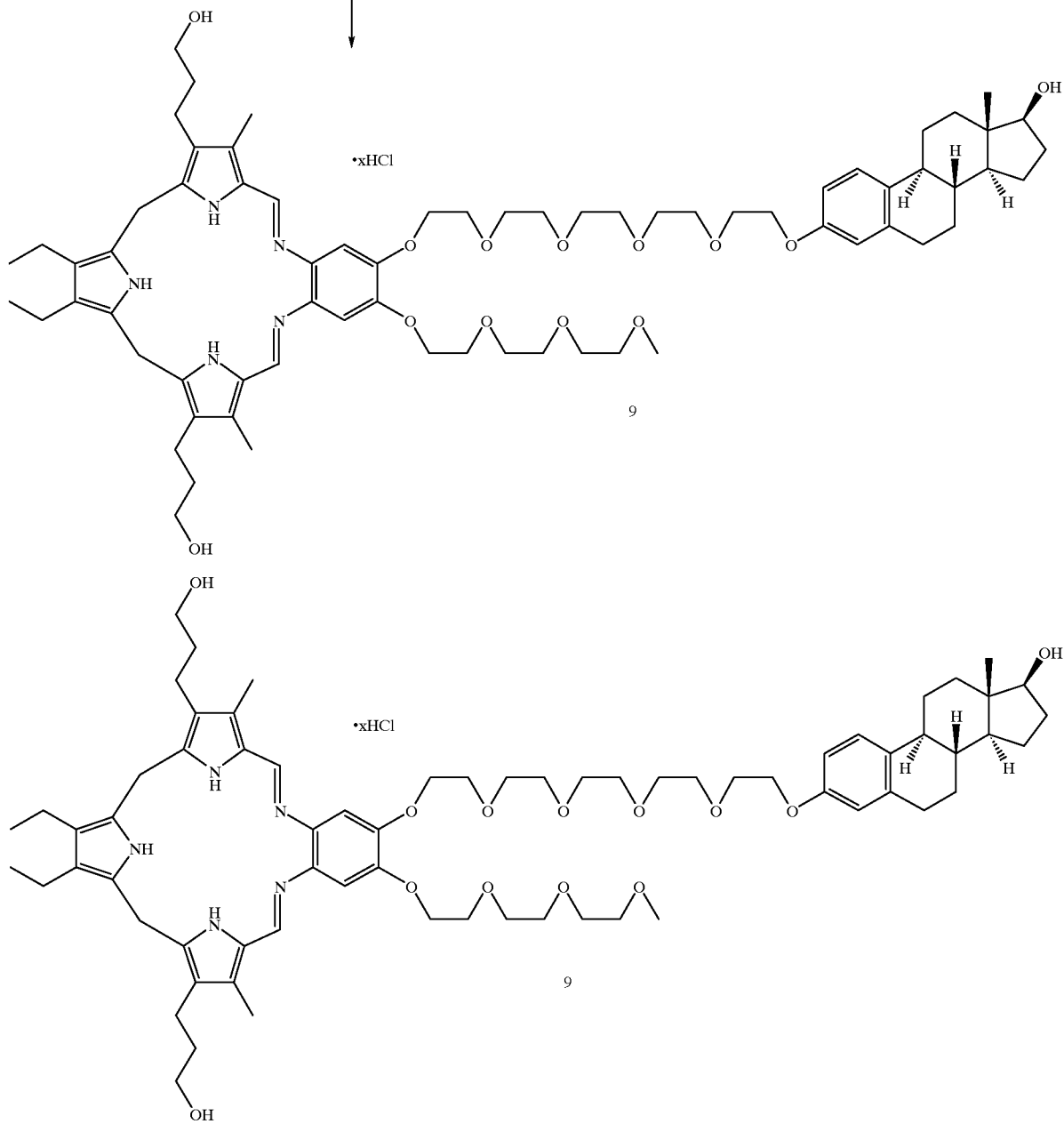

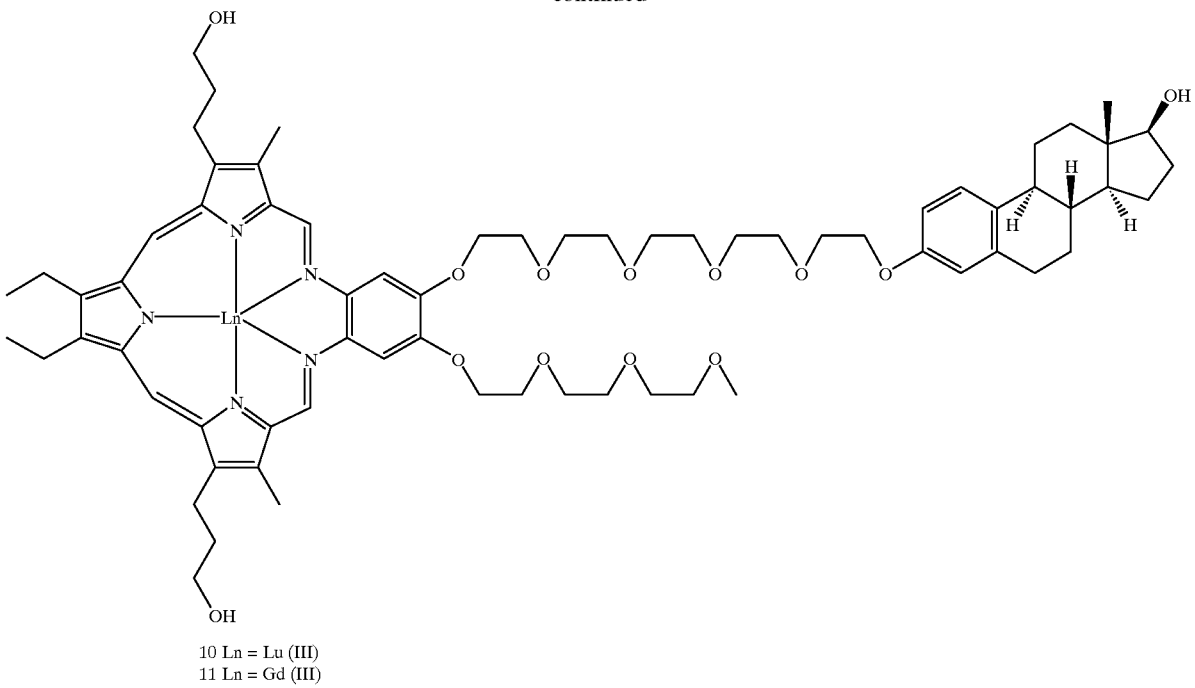

10 Ln = Lu (III)
11 Ln = Gd (III)

3-(2-(Ethoxy-2-(ethoxy-2-(ethoxy-(2-(1-oxy-2-(2-(ethoxy-2-(ethoxy-(2-methoxy)))ethoxy)4,5-dinitrobenzene)ethoxy))))ethoxy)-17βhydroxy-3-oxy-1,3,5(10)-esratriene (6). The iodide 4 (500 mg) and the sodium salt of 1-hydroxy-2-(2-(ethoxy-2-(ethoxy-(2-methoxy)))ethoxy)-4,5-dinitrobenzene 5 (336 mg, 1.1 eq.) and acetonitrile (5 mL) were combined in a flask and the reaction mixture was heated at reflux overnight. Potassium carbonate (126 mg, 1.1 eq.) was added, and heating continued for ca. four hours. The reaction mixture was transferred to a separatory funnel with CHCl₃ (ca 25 mL), washed with water (2×15 mL), solvent removed on a rotary evaporator, and the residue dried overnight in vacuo. The crude product was purified by silica gel chromatography using 2% MeOH in CHCl₃ as eluent. Fractions containing only product were combined, solvent was removed by rotary evaporation, and the residue dried in vacuo to give 6 as a yellowish solid (549 mg, 80.5%). FAB: MH$^+$821.

Using known chemistry for the synthesis of texaphyrins (see the texaphyrin patents previously incorporated by reference herein) the dinitro compound 6 was reduced to the diamine 7 using an atmospheric pressure hydrogenation with 10% Pd on charcoal and 2 eq. of conc. HCl. The reduction was usually complete in 1–2 h. Afterwards, the catalyst was filtered off using a pad of Celite, the diamine solution was diluted with methanol, 1 equivalent of diformyl tripyrrane 8 was added, and the reaction was heated to reflux under nitrogen. The reaction started immediately after the addition of diformyl tripyrrane and was usually complete in 1–3 hr. Proton and carbon NMR of the resulting non-aromatic macrocycle 9 was consistent with structure. The nonaromatic macrocycle 9 was oxidatively metallated using 1.5 equiv.s of either lutetium acetate or gadolinium acetate and 10 equiv.s of triethylamine under air atmosphere to give the lutetium estradiol complex 10 (in 38% yield with a relative purity of 89%) or the gadolinium estradiol complex 11 (in 47% yield with a relative purity of 91%), respectively.

The synthesis of a texaphyrin-cholesterol conjugate is carried out in a similar manner using cholesterol instead of estradiol.

Example 2

Loading Red Blood Cells with a Texaphyrin-Lipophilic Molecule Conjugate

The present example provides for the loading of red blood cells with a texaphyrin-estradiol conjugate. Red blood cells (RBC's) were successfully loaded with gadolinium texaphyrin-estradiol conjugate 11 ("GTE") following an osmotic challenge to the red blood cells. Subsequently, UV/Vis spectra revealed that most of the conjugate was contained within the cell wall of the red blood cells.

For the studies below, the following general procedure was used: Whole blood from rabbit was collected in the presence of heparin and centrifuged. The serum layer was removed, and the RBC's were resuspended in saline (138 mM NaCl), and washed three times. After the third wash, the pelleted RPC's were resuspended in hypertonic saline (268 mM NaCl). The cells were mixed gently, held approximately 3 min at room temperature, and centrifuged. The pelleted RBC's were resuspended in three volumes of hypotonic saline (110 mM NaCl) containing GTE to give Gd texaphyrin-estradiol-red blood cell complex.

I. In a first study, 300 mL of pelleted RBC's were resuspended in 1.0 mL of 110 mM NaCl with 0.2 or 0.4 mmoles of GTE. The cells were mixed gently and sonicated. After three washes, the pellet of GTE-RBC complex (300 mL) was resuspended with saline to a total volume of 2.0 mL. To determine the GTE content, 750 mL of this 2.0 mL solution were removed, 250 mL of fresh saline was added, and the optical density was read on a spectrophotometer. A control cuvette contained an equivalent mass and volume of RBC's treated similarly but without GTE. The O.D. of the 2.0 mL solution was 0.9859, which indicated a yield of 120 mg total GTE complex (T2BET2, 732 nm, a 15.35 mg/mL solution has an O.D. of 0.3291).

II. In a second study, two different amounts of a stock solution of 2 mM GTE in 5% mannitol were used; 1.6 mL with 4.0 mL packed RBC's, and 6.6 mL with 5.5 mL packed RBC's. To prepare the respective complexes, the RBC's were washed as described previously, the respective volumes of RBC's were resuspended with hypertonic saline to a total volume of 50 mL and centrifuged. The supernatant was removed and solutions of hypotonic saline with GTE were added so as to keep the volume at 40 mL. The suspensions were treated as described above and the final washed RBC's were suspended in a volume of 15 mL with normal saline and transferred to 100×17 mm tubes to be analyzed by MRI (see, Example 3) (for the 1.6 mL reaction, 11 mL of saline; for the 6.6 mL reaction, 9.5 mL of saline; the control was 5.0 mL packed RBC's and 10 mL of saline).

III. In a further study, RBC's were loaded with GTE to be used as an injectable into rabbits. Packed RBC's (5.0 mL, washed as described) were treated with hypertonic saline and 40 mL total volume of hypotonic saline with 6.0 mL GTE. After sonication, the cells were washed 3 times and resuspended with 2.5 mL of normal saline. The resulting complex was used for injection into rabbits (see, Example 4).

Example 3

In Vitro Imaging with GdT2BET-Estradiol-Red Blood Cell Complex

The present example provides in vitro magnetic resonance imaging (MRI) results with GTE-RBC complex.

Packed or resuspended red blood cell complexes were imaged using a GE 0.5T Signa magnetic resonance imager (GE Medical Systems, Milwaukee, Wis.) and the following parameters: pulse sequences, spin echo 350/15; acquisition parameters, 20FOV, 256×256; slice thickness/space, 5 mm/12.5 mm; and nex; 2.

Table 2 provides MRI values using GTE-RBC complex (from Example 2, II). $CuSO_4$ is an imaging standard that allows the intensity (whiteness) of the signal to be gauged.

TABLE 2

MRI Values of GdT2BET-Estradiol-Red Blood Cell Complexes

| Sample | RBC Control | RBC with 3.2 mmol GTE | RBC with 13.2 mmol GTE | Saline control | $CuSO_4$ Standard |
|---|---|---|---|---|---|
| Packed | 818 | 1386 | 1405 | 311 | 1181 |
| GTE-RBC Complexes | 793 | 1354 | 1514 | 309 | 1166 |
| Average | 805.5 | 1370 | 1459.5 | 310 | 1173.5 |
| Resuspended | 530 | 876 | 2095 | 298 | 1144 |
| GTE-RBC Complexes | 496 | 800 | 2084 | 280 | 1103 |
| | 487 | 793 | 2105 | 270 | 1095 |
| Average | 504.333333 | 823 | 2094.666667 | 282.67 | 1114 |

Approximately 8.3 $\mu$mol GTE was incorporated in 5 ml of packed red cells using this method.

Example 4

In Vivo Imaging with GdT2BET-Estradiol-Red Blood Cell Complex

The present example demonstrates magnetic resonance imaging of an animal using GTE-RBC complexes. MRI scans revealed contrast enhancement of tissues and enhanced angiograms for up to 30 min after injection.

A New Zealand white rabbit (2.72 kg) having a V2 carcinoma tumor implanted in each thigh. was injected with 7 mL of GTE-RBC complex and a normal New Zealand white rabbit (3 kg) was also injected with the same amount of the complex as a control. The rabbit having the tumors died after 2.5 mL of the complex was injected. The rabbit appeared to be already very sick from the cancer. The normal rabbit was scanned precontrast, immediately post-injection, and 30 min after injection. The rabbit was positioned supine inside a knee coil and entered the magnetic field feet first. The rabbit was anesthetized and maintained with ketamine/Rompun cocktail during MRI. The scan parameters were as in Example 3 with the acquisition parameter being 256×160 for this animal study and the MR angiogram scanning technique was 2D TOF for the aorta.

The normal rabbit had good liver and angiogram enhancement for at least 30 min after injection of the GTE-RBC complex.

Example 5

Photodynamic Therapy Using Photosensitive Texaphyrin-Lipophilic Molecule-Loaded-Vesicles The present example provides for the light-dependent lysis of loaded vesicles, such as red blood cells or liposomes, and the consequent deposition of the contents at the irradiated site. When irradiated with light of an appropriate wavelength, vesicles loaded with a photosensitive texaphyrin will lyse.

The effect of PDT with photosensitive texaphyrin-loaded vesicles is multifaceted in that specificity is provided by the biolocalization of the vesicle, a PDT effect is seen in the vicinity of the deposited texaphyrin due to singlet oxygen product toxicity, and if a therapeutic agent is incorporated into the vesicle in addition to the texaphyrin, the therapeutic agent is deposited at a target site. A chemotherapeutic drug may be delivered to a target site in this manner, for example.

A preferred photosensitive texaphyrin is a lutetium texaphyrin, for example, compound $1_B$ as described herein.

In the present light-dependent lysis, the light may have a wavelength range of about 650–900 nm, preferably 700–800 nm, and most preferably 730–770 nm.

Example 6

Liposomes Comprising a Texaphyrin-Lipophilic Molecule Conjugate

The present example provides for the incorporation of a texaphyrin-lipophilic molecule conjugate into liposomes and liposomal-like particles.

A texaphyrin-lipophilic molecule conjugate may be incorporated into small unilamellar liposomes as follows, for example. Egg phosphatidylcholine conjugated with ethylene glycol and cholesterol (8:2 molar ratio) are suspended in chloroform and a 33% molar concentration of texaphyrin-lipophilic molecule conjugate is added to the solution. The chloroform is evaporated under vacuum and the dried material is resuspended in phosphate buffered saline (PBS). The mixture is transferred to a cryovial, quick frozen in liquid nitrogen, and thawed five times. The material is then extruded through an extruder device (Lipex Biomembranes, Vancouver, B.C., Canada) 10 times using a 400 nm diameter pore size polycarbonate filter to produce 400 nm liposomes. A portion of the 400 nm liposomes is extruded through 100 nm diameter filters 10 times to produce 100 nm liposomes. A portion of the 100 nm liposomes is then extruded 10 times through 15 nm filters, producing liposomes of 30 nm size.

Liposomes prepared as described above may also be subjected to a Microfluidizer (Microfluidics, Newton, Mass.). Specifically, liposomes may be passed 10 times through the microfluidizer at a pressure of 16,000 psi and a flow rate of 450 mL/min. The resulting liposomes are expected to have a mean average size of 30–40 nm, which may be verified by Quasi Elastic Light Scattering.

A texaphyrin-lipophilic molecule conjugate incorporated in this way into liposomes may be physically inside the liposome, incorporated into the lipid bilayer of the liposome, or incorporated in such a way that part of the conjugate is outside of the liposome. A liposome incorporating a texaphyrin-lipophilic molecule can be stabilized using ethylene glycol to slow its uptake by phagocytic white blood cells.

Example 7

Induction of Antibody Formation Using Texaphyrin-Lipophilic Molecule-Loaded-Red Blood Cells or -Liposomes In addition to conventional methods known to those of skill in the art of immunology for making antibodies having a particular binding specificity, antibodies having binding specificity for a texaphyrin molecule may be induced in a host that has been administered a texaphyrin-lipophilic molecule loaded-red blood cell or -liposome. Further, if the loaded cell also contains an immunogen, antibodies may be generated having binding specificity for that immunogen.

Using a photosensitive texaphyrin, light will lyse such a loaded red blood cell or liposome causing release of its contents within a host. Consequent exposure of the host to an immunogen contained therein would induce antibody formation to the immunogen. Candidate immunogens may include, but are not limited to, surface HIV proteins, such as gp 120, for example. This method would be particularly effective using a loaded cell from an animal different than the animal injected, for example, using loaded goat red blood cells for injection into a rabbit. The goat cells may act as adjuvant in this case.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved, All such similar substitutes and modifications apparent to those skilled in the art are deemed to be within the spirit, scope and concept of the invention as defined by the appended claims.

What is claimed is:

1. A texaphyrin-lipophilic molecule-vesicle complex comprising a vesicle loaded with a texaphyrin-lipophilic molecule conjugate wherein the lipophilic molecule portion of the complex is estradiol or cholesterol.

2. A texaphyiin-lipophilic molecule-vesicle complex comprising a vesicle loaded with a texaphyrin-lipophilic molecule conjugate wherein the texaphyrin-lipophilic molecule portion of the complex has structure I:

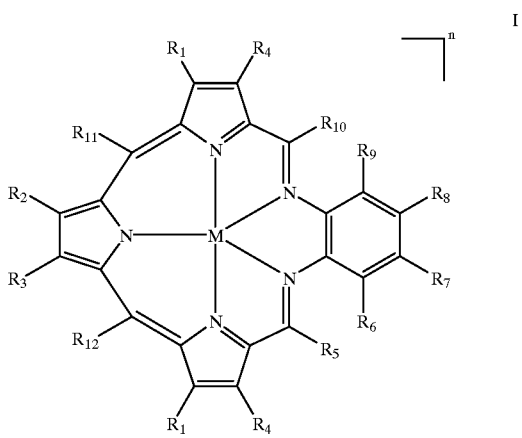

wherein

M is a divalent or trivalent metal cation;

$R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a lipophilic molecule, or a linker that is linked to a lipophilic molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carbokyamide, carboxyamidealkyl, amino, aminoalkyl, or a linker that is linked to a saccharide, or to a lipophilic molecule;

n is an integer value less than or equal to 5; and wherein at least one of $R_1$–$R_{12}$ is a lipophilic molecule or a linker that is linked to a lipophilic molecule.

3. A texaphyrin-lipophilic molecule-vesicle complex comprising a vesicle loaded with a texaphyrin-lipophilic molecule conjugate wherein the texaphyrin-lipophilic molecule portion of the complex has structure II:

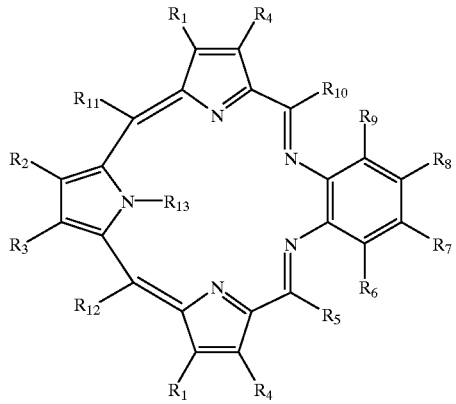

II wherein $R_1$–$R_4$, $R_7$ and $R_8$ are independently hydrogen, halide, hydroxyl, alkyl, alkenyl, alkynyl, aryl, haloalkyl, nitro, formyl, acyl, hydroxyalkyl, alkoxy, hydroxyalkoxy, hydroxyalkenyl, hydroxyalkynyl, saccharide, carboxy, carboxyalkyl, carboxyamide, carboxyamidealkyl, amino, aminoalkyl, a lipophilic molecule, or a linker that is linked to a lipophilic molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, alkenyl, alkynyl, aryl, hydroxyalkyl, alkoxy, hydroxyalkoxy, hydroxyalkenyl, hydroxyalkynyl, carboxyalkyl, carboxyamide, carboxyamidealkyl, amino, aminoalkyl, or a linker that is linked to a saccharide, or to a lipophilic molecule;

$R_{13}$ is alkyl, alkenyl, oxyalkyl, or hydroxyalkyl having up to about 3 carbon atoms and having rotational flexibility around a first-bound carbon atom; and wherein at least one of $R_1$–$R_{12}$ is a lipophilic molecule or a linker that is linked to a lipophilic molecule.

4. The complex of claim 2 wherein $R_1$ is $CH_2(CH_2)_2OH$, $R_2$ and $R_3$ are $CH_2CH_3$, $R_4$ is $CH_3$, $R_7$ is $O(CH_2CH_2)_3CH_3$, $R_8$ is a linker that is linked to estradio, and $R_5$, $R_6$, and $R_9$–$R_{12}$ are H.

5. The complex of claim 2 wherein $R_1$ is $CH_2(CH_2)_2OH$, $R_2$ and $R_3$ are $CH_2CH_3$, $R_4$ is $CH_3$, $R_7$ is $O(CH_2CH_2)_3CH_3$, $R_8$ is a linker that is linked to cholesterol, and $R_5$, $R_6$, and $R_9$–$R_{12}$ are H.

6. A texaphyrin-lipophilic molecule-vesicle complex comprising a vesicle loaded with a texaphyrin-lipophilic molecule conjugate wherein the texaphyrin-lipophilic molecule conjugate has structure I:

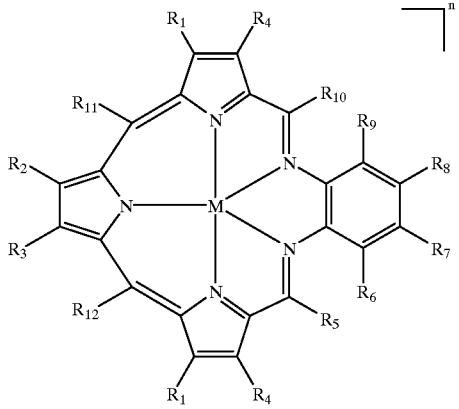

I wherein M is a divalent or trivalent metal cation; $R_1$ is hydroxyalkyl; $R_2$, $R_3$ and $R_4$ are alkyl; $R_7$ is alkoxy; $R_8$ is a linker that is linked to a lipophilic molecule; $R_5$, $R_6$, and $R_9$–$R_{12}$ are hydrogen; and n is an integer value less than or equal to 5.

7. The complex of claim 6 wherein $R_1$ is $CH_2(CH_2)_2OH$, $R_2$ and $R_3$ are $CH_2CH_3$, $R_4$ is $CH_3$, $R_7$ is $O(CH_2CH_2O)_3CH_3$, and $R_8$ is a linker that is linked to estradiol.

8. The complex of claim 6 wherein the vesicle portion of the complex is a biological cell.

9. The complex of claim 8 wherein the biological cell is a red blood cell.

10. The complex of claim 6 wherein the vesicle portion of the complex is a liposome.

11. The complex of claim 6 wherein M is Lu(III) or Gd(III).

12. A texaphyrin-lipophilic molecule-vesicle complex comprising a vesicle loaded with a texaphyrin-lipophilic molecule conjugate wherein the texaphyrin-lipophilic molecule conjugate has structure I:

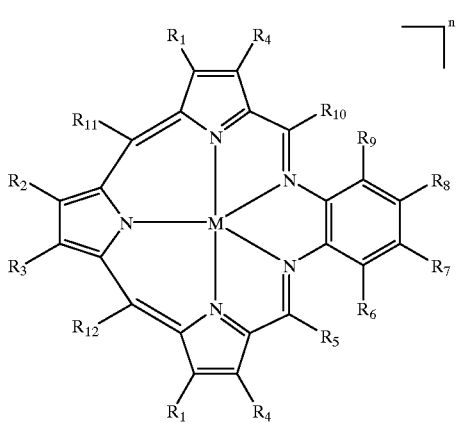

I wherein M is a divalent or trivalent metal cation; $R_1$ is $CH_2(CH_2)_2OH$; $R_2$ and $R_3$ are $CH_2CH_3$; $R_4$ is $CH_3$; $R_7$ is $O(CH_2CH_2O)_3CH_3$; $R_8$ is a linker that is linked to estradiol; $R_5$, $R_6$, and $R_9$–$R_{12}$ are hydrogen; and n is an integer value less than or equal to 5.

13. The complex of claim 12 wherein the vesicle portion of the complex is a red blood cell.

14. The complex of claim 12 wherein the vesicle portion of the complex is a liposome.

15. The complex of claim 12 wherein M is Lu(III) or Gd(III).

16. A texaphyrin-lipophilic molecule-vesicle complex comprising a vesicle loaded with a texaphyrin-lipophilic molecule conjugate wherein the texaphyrin-lipophilic molecule conjugate has structure I:

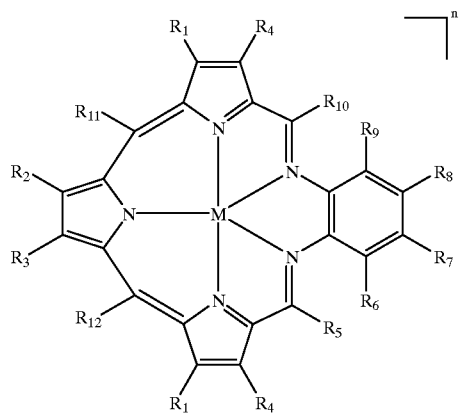

wherein M is a divalent or trivalent metal cation; $R_1$ is $CH_2(CH_2)_2OH$; $R_2$ and $R_3$ are $CH_2CH_3$; $R_4$ is $CH_3$; $R_7$ is $O(CH_2CH_2O)_3CH_3$; $R_8$ is a linker that is linked to cholesterol; $R_5$, $R_6$, and $R_9$–$R_{12}$ are hydrogen; and n is an integer value less than or equal to 5.

17. The complex of claim 16 wherein the vesicle portion of the complex is a red blood cell.

18. The complex of claim 16 wherein the vesicle portion of the complex is a liposome.

19. The complex of claim 16 wherein M is Lu(III) or Gd(III).

* * * * *